United States Patent
Eidenschink et al.

(10) Patent No.: US 9,763,778 B2
(45) Date of Patent: Sep. 19, 2017

(54) AORTIC INSUFFICIENCY VALVE PERCUTANEOUS VALVE ANCHORING

(71) Applicant: St. Jude Medical, Cardiology Division, Inc., St. Paul, MN (US)

(72) Inventors: Tracee Eidenschink, Wayzata, MN (US); Ryan Buesseler, Delano, MN (US); Sounthara Khouengboua, Chaska, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 14/660,028

(22) Filed: Mar. 17, 2015

(65) Prior Publication Data

US 2015/0265400 A1 Sep. 24, 2015

Related U.S. Application Data

(60) Provisional application No. 61/954,777, filed on Mar. 18, 2014.

(51) Int. Cl.
*A61F 2/06* (2013.01)
*A61F 2/24* (2006.01)
(Continued)

(52) U.S. Cl.
CPC ........ *A61F 2/2409* (2013.01); *A61B 17/0644* (2013.01); *A61F 2/2418* (2013.01); *A61B 17/068* (2013.01); *A61B 2017/00243* (2013.01); *A61B 2017/00783* (2013.01); *A61B 2017/00867* (2013.01); *A61B 2017/0648* (2013.01); *A61B 2017/0649* (2013.01); *A61B 2090/08021* (2016.02); *A61F 2/2436* (2013.01);
(Continued)

(58) Field of Classification Search
CPC .... A61F 2/2418; A61F 2/2433; A61F 2/2436; A61F 2/2439
USPC .......... 623/1.11, 1.15, 1.24, 1.26, 2.14, 2.18, 623/2.11; 606/191, 192, 194, 198
See application file for complete search history.

(56) References Cited

U.S. PATENT DOCUMENTS 3,657,744 A 4/1972 Ersek
4,275,469 A 6/1981 Gabbay
(Continued)

FOREIGN PATENT DOCUMENTS

CN 103190968 A 7/2013
DE 19857887 A1 7/2000
(Continued)

OTHER PUBLICATIONS

Extended European Search Report for Application No. 15159320.9 dated Aug. 10, 2015.
(Continued)

*Primary Examiner* — Alvin Stewart
(74) *Attorney, Agent, or Firm* — Lerner, David, Littenberg, Krumholz & Mentlik, LLP

(57) ABSTRACT

An anchoring device for use within a cardiovascular structure includes an expandable ring having a central axis extending in a longitudinal direction. At least one leg extends from the ring in the longitudinal direction. The leg includes a first end connected to the ring and a free end, with at least one anchor connected to the leg. The anchoring device may be used to anchor a transcatheter heart valve within the cardiovascular structure.

19 Claims, 20 Drawing Sheets

(51) Int. Cl.
*A61B 17/064* (2006.01)
*A61B 17/068* (2006.01)
*A61B 17/00* (2006.01)
*A61B 90/00* (2016.01)

(52) U.S. Cl.
CPC ............... *A61F 2210/0061* (2013.01); *A61F 2220/0025* (2013.01); *A61F 2230/0013* (2013.01); *A61F 2230/0069* (2013.01); *A61F 2250/006* (2013.01); *A61F 2250/0069* (2013.01)

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,480,423 A | 1/1996 | Ravenscroft et al. | |
| 5,843,164 A * | 12/1998 | Frantzen | A61F 2/07 623/1.16 |
| 5,843,167 A * | 12/1998 | Dwyer | A61F 2/07 623/1.14 |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 * | 4/2001 | Letendre | A61F 2/07 623/1.11 |
| 6,221,096 B1 * | 4/2001 | Aiba | A61F 2/86 606/108 |
| 6,264,691 B1 | 7/2001 | Gabbay | |
| 6,267,783 B1 * | 7/2001 | Letendre | A61F 2/07 623/1.11 |
| 6,299,637 B1 * | 10/2001 | Shaolian | A61F 2/2418 623/1.24 |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,503,272 B2 * | 1/2003 | Duerig | A61F 2/2418 623/1.24 |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 * | 9/2003 | Thompson | A61F 2/91 606/108 |
| 6,685,625 B2 | 2/2004 | Gabbay | |
| 6,685,739 B2 * | 2/2004 | DiMatteo | A61F 2/2412 623/1.24 |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 * | 11/2004 | Thompson | A61F 2/91 623/1.11 |
| 6,830,584 B1 | 12/2004 | Seguin | |
| 6,843,802 B1 * | 1/2005 | Villalobos | A61F 2/954 606/198 |
| 6,869,444 B2 | 3/2005 | Gabbay | |
| 6,893,460 B2 | 5/2005 | Spenser et al. | |
| 6,908,481 B2 | 6/2005 | Cribier | |
| 6,936,058 B2 * | 8/2005 | Forde | A61B 17/0057 606/108 |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,175,656 B2 * | 2/2007 | Khairkhahan | A61F 2/2403 606/200 |
| 7,195,641 B2 * | 3/2007 | Palmaz | A61F 2/2418 623/1.26 |
| 7,201,772 B2 * | 4/2007 | Schwammenthal | A61F 2/2418 623/1.24 |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 * | 6/2008 | Schreck | A61F 2/2418 623/1.26 |
| 7,452,371 B2 | 11/2008 | Pavcnik et al. | |
| 7,510,572 B2 | 3/2009 | Gabbay | |
| 7,524,331 B2 | 4/2009 | Birdsall | |
| 7,527,645 B2 * | 5/2009 | Perez | A61F 2/07 623/1.12 |
| RE40,816 E | 6/2009 | Taylor et al. | |
| 7,585,321 B2 | 9/2009 | Cribier | |
| 7,682,390 B2 | 3/2010 | Seguin | |
| 7,722,666 B2 * | 5/2010 | Lafontaine | A61F 2/2418 623/2.11 |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| 7,988,724 B2 * | 8/2011 | Salahieh | A61B 17/0644 623/2.12 |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| 8,092,520 B2 * | 1/2012 | Quadri | A61F 2/2418 623/1.26 |
| D654,169 S | 2/2012 | Braido | |
| D654,170 S | 2/2012 | Braido et al. | |
| 8,133,251 B2 * | 3/2012 | Ravenscroft | A61F 2/01 604/95.02 |
| D660,432 S | 5/2012 | Braido | |
| D660,433 S | 5/2012 | Braido et al. | |
| D660,967 S | 5/2012 | Braido et al. | |
| 8,211,165 B1 * | 7/2012 | McIntosh | A61F 2/2475 623/1.24 |
| 8,226,701 B2 * | 7/2012 | Glynn | 623/1.11 |
| 8,251,067 B2 * | 8/2012 | Hendricksen | A61B 17/12022 128/200.26 |
| 8,348,988 B2 * | 1/2013 | Lad | A61F 2/07 623/1.13 |
| 8,562,638 B2 * | 10/2013 | Sokolov | A61F 2/01 606/200 |
| 8,628,571 B1 * | 1/2014 | Hacohen | A61F 2/2403 623/1.26 |
| 8,834,551 B2 * | 9/2014 | McGuckin, Jr. | A61F 2/2418 623/1.11 |
| 8,926,680 B2 * | 1/2015 | Ferrera | A61B 17/12022 623/1.11 |
| 8,932,343 B2 * | 1/2015 | Alkhatib | A61F 2/2418 623/1.15 |
| 9,198,687 B2 * | 12/2015 | Fulkerson | A61B 17/221 |
| 2002/0036220 A1 | 3/2002 | Gabbay | |
| 2002/0123802 A1 * | 9/2002 | Snyders | A61F 2/2418 623/2.18 |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0019374 A1 * | 1/2004 | Hojeibane | A61F 2/2412 623/1.13 |
| 2004/0049262 A1 | 3/2004 | Obermiller et al. | |
| 2004/0093075 A1 | 5/2004 | Kuehne | |
| 2004/0127982 A1 * | 7/2004 | Machold | A61F 2/2418 623/2.36 |
| 2004/0210304 A1 | 10/2004 | Seguin et al. | |
| 2004/0220655 A1 * | 11/2004 | Swanson | A61F 2/2487 623/1.11 |

(56) References Cited

U.S. PATENT DOCUMENTS

| | | |
|---|---|---|
| 2005/0096726 A1 | 5/2005 | Sequin et al. |
| 2005/0096735 A1* | 5/2005 | Hojeibane ............ A61F 2/2418 623/1.24 |
| 2005/0125051 A1 | 6/2005 | Eidenschink et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2006/0008497 A1 | 1/2006 | Gabbay |
| 2006/0020321 A1 | 1/2006 | Parker |
| 2006/0025857 A1* | 2/2006 | Bergheim ............ A61F 2/2409 623/2.18 |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0255386 A1 | 11/2007 | Tenne |
| 2007/0288087 A1 | 12/2007 | Fearnot et al. |
| 2008/0004696 A1 | 1/2008 | Vesely |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255661 A1* | 10/2008 | Straubinger .......... A61F 2/2427 623/2.36 |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0062901 A1* | 3/2009 | McGuckin, Jr. ...... A61F 2/2418 623/1.15 |
| 2009/0082841 A1* | 3/2009 | Zacharias ............ A61F 2/95 623/1.11 |
| 2009/0082847 A1* | 3/2009 | Zacharias ............ A61F 2/82 623/1.15 |
| 2009/0112309 A1 | 4/2009 | Jaramillo et al. |
| 2009/0138079 A1 | 5/2009 | Tuval et al. |
| 2009/0306622 A1 | 12/2009 | Machold et al. |
| 2009/0319037 A1* | 12/2009 | Rowe ................... A61F 2/2418 623/2.11 |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1* | 2/2010 | Alon .................... A61F 2/2418 623/2.11 |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1* | 7/2010 | Braido ................. A61F 2/2418 623/1.26 |
| 2010/0185277 A1* | 7/2010 | Braido ................. A61F 2/2412 623/2.18 |
| 2010/0191326 A1 | 7/2010 | Alkhatib |
| 2010/0204781 A1* | 8/2010 | Alkhatib ............... A61F 2/2418 623/1.26 |
| 2010/0204785 A1* | 8/2010 | Alkhatib ............... A61F 2/2418 623/2.37 |
| 2010/0217382 A1 | 8/2010 | Chau et al. |
| 2010/0249911 A1 | 9/2010 | Alkhatib |
| 2010/0249923 A1* | 9/2010 | Alkhatib ............... A61F 2/2418 623/2.18 |
| 2010/0286768 A1 | 11/2010 | Alkhatib |
| 2010/0298931 A1* | 11/2010 | Quadri ................. A61F 2/2418 623/2.11 |
| 2011/0029072 A1 | 2/2011 | Gabbay |
| 2011/0245911 A1* | 10/2011 | Quill ................... A61F 2/2418 623/1.26 |
| 2012/0022633 A1* | 1/2012 | Olson .................. A61F 2/2418 623/1.11 |
| 2012/0078347 A1* | 3/2012 | Braido ................. A61F 2/2418 623/1.26 |
| 2013/0325103 A1* | 12/2013 | Arai .................... A61F 2/2418 623/1.24 |
| 2014/0228940 A1* | 8/2014 | McKinnis ............. A61F 2/2475 623/1.24 |
| 2014/0277389 A1* | 9/2014 | Braido ................. A61F 2/2418 623/1.26 |
| 2015/0265400 A1* | 9/2015 | Eidenschink ........ A61B 17/0644 623/2.18 |
| 2015/0342738 A1* | 12/2015 | McKinnis ............. A61F 2/2475 623/1.24 |

FOREIGN PATENT DOCUMENTS

| | | |
|---|---|---|
| DE | 10121210 A1 | 11/2002 |
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| FR | 2847800 A1 | 6/2004 |
| FR | 2850008 A1 | 7/2004 |
| WO | 9117720 B1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007071436 A2 | 6/2007 |
| WO | 2008070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

Andersen, Henning Rud, Transluminal Catheter Implanted Prosthetic Heart Valves, International Journal of Angiology 7:102-106 (1998).

Catheter-implanted prosthetic heart valves, Knudsen, L.L., et al., The International Journal of Artificial Organs, vol. 16, No. 5 1993, pp. 253-262.

Is It Reasonable to Treat All Calcified Stenotic Aortic Valves With a Valved Stent?, 579-584, Zegdi, Rachid, MD, PhD et al., J. of the

(56) References Cited

OTHER PUBLICATIONS

American College of Cardiology, vol. 51, No. 5, Feb. 5, 2008.
Quaden, René et al., "Percutaneous aortic valve replacement: resection before implantation," 836-840, European J. of Cardio-thoracic Surgery 27 (2005).
Ruiz, Carlos, "Overview of PRE-CE Mark Transcatheter Aortic Valve Technologies", Euro PCR, May 25, 2010.
Transluminal Aortic Valve Placement, Moazami, Nader, et al., ASAIO Journal, 1996; 42:M381-M385.
Transluminal implantation of artificial heart valves, Andersen, H. R., et al., European Heart Journal (1992) 13, 704-708.
U.S. Appl. No. 29/375,243, filed Sep. 20, 2010.
U.S. Appl. No. 29/375,260, filed Sep. 20, 2010.

* cited by examiner

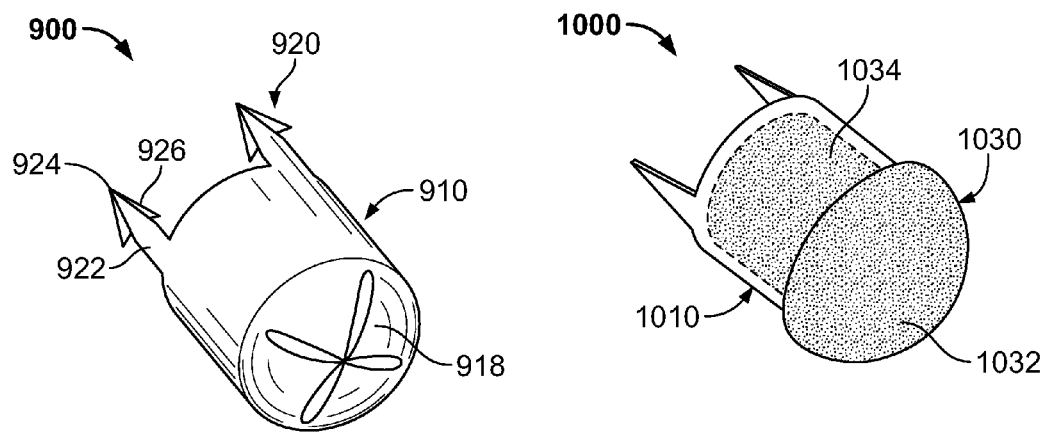
FIG. 12
FIG. 13
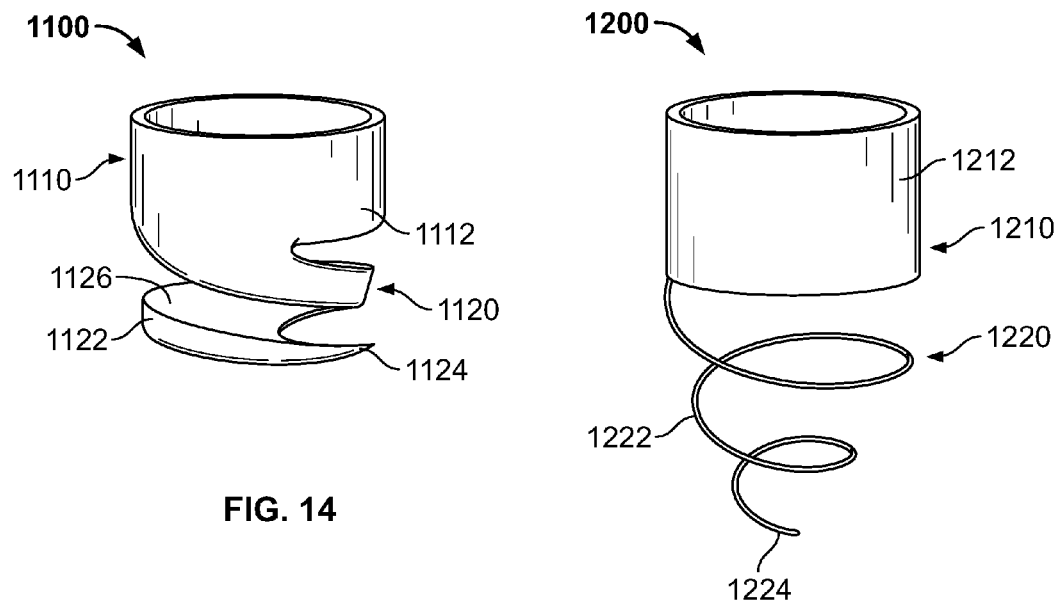
FIG. 14
FIG. 15

AORTIC INSUFFICIENCY VALVE PERCUTANEOUS VALVE ANCHORING

CROSS-REFERENCE TO RELATED APPLICATION

The present application claims the benefit of the filing date of U.S. Provisional Patent Application No. 61/954,777 filed Mar. 18, 2014, the disclosure of which is hereby incorporated herein by reference.

BACKGROUND OF THE INVENTION

The present disclosure generally pertains to anchoring devices that can be used in connection with a transcatheter valve prosthesis.

Heart valve disease may either be congenital or develop over a period of time and often materializes without notice. Where possible, patients are monitored and instructed to make lifestyle changes. However, where the function of the valve becomes significantly impaired, the only option may be heart valve replacement or repair.

There are two general types of heart valve replacement procedures. The first type is surgical replacement where the patient is placed on a heart and lung machine to undergo open heart surgery. The heart is stopped so that the diseased valve may be surgically removed and replaced by a prosthetic valve that may be sutured or otherwise implanted into the same general location. This type of procedure is often the first consideration because of its long-term efficacy. However, open heart surgery is highly invasive and includes many attendant risks with the potential to be very severe or life threatening. Aside from the physical trauma of invading one of the most crucial areas of the human body, the risks are compounded by the heart and lung machine, which, among other things, can damage red blood cells leading to neurological deficiencies.

Due to these attendant risks, surgical valve replacement may not be a viable option, particularly for the elderly and frail. Additionally, individuals who receive surgical replacements earlier in life may need to have a follow-up replacement, which would likely be performed at an age where open heart surgery may be too risky. Thus, transcatheter valve implantation may be the best approach as the other type of heart valve replacement procedure. Transcatheter valve implantation is generally achieved by guiding, often percutaneously, a catheter which retains an expandable prosthetic valve, through a patient's cardiovascular system to the target, diseased valve. The prosthetic valve is deployed such that the diseased valve is pushed out of the way so that the prosthetic valve can take over. Expandable prosthetic valves are primarily comprised of porcine or bovine tissue that is sewn to a stent that includes struts forming individually expandable cells. The stent may be made from a shape memory metal, such as Nitinol, which gives it a natural bias toward an expanded state in order to hold the prosthetic valve in place.

Transcatheter valve implantation is currently indicated only for patients with severe stenosis. The primary reason for this limitation is valve migration/embolization. While the natural bias of the stent helps exert significant radial force against the surrounding soft tissue, this radial force typically is not enough to counteract the force of blood flow and gyrations from the beating heart. Thus, transcatheter valve implantation is indicated only for severe cases of stenosis so that the stent has a stable anchoring structure, such as calcium or plaque deposits, along the soft tissue of the native heart valve. Patients with congenital defects, sclerosis and/or stenosis without sufficient build-up of calcium or other deposits for anchoring the transcatheter valve may not qualify for either type of valve replacement procedure yet may suffer from valvular insufficiency.

BRIEF SUMMARY OF THE INVENTION

Disclosed herein are anchoring devices and methods for implanting an anchoring device for use in conjunction with a transcatheter device, such as a transcatheter prosthetic valve, in a patient's circulatory system.

In one aspect of the present disclosure, an anchoring device for use within a cardiovascular structure may include an expandable ring having a central axis extending in a longitudinal direction; a support structure extending from the expandable ring in the longitudinal direction; and at least one anchor coupled to the support structure and extending radially inwardly from the support structure toward the central axis.

In another aspect, an anchoring device for use within a cardiovascular structure may include a cylindrical body having a first end, a second end, and a central axis extending in a longitudinal direction; and a mooring structure extending from the second end of the cylindrical body. The mooring structure may include a penetrating point adapted to penetrate soft tissue and an anti-back-out feature disposed between the penetrating point and the second end of the cylindrical body.

In a further aspect of the present disclosure, an anchoring device for use within a cardiovascular structure may include an expandable ring having a central axis extending in a longitudinal direction. The support structure may extend from the expandable ring in the longitudinal direction and may include at least one attachment portion. The anchoring device may also include at least one anchor connected to the at least one attachment portion.

In yet another aspect, an anchoring device for use within a cardiovascular structure may include a length of wire having a first portion with a free end, a loop formed at an end opposite the free end, and a sliding structure slidably connecting the loop to the first portion; and at least one anchor coupled to the length of wire along the loop, wherein a size of the loop is adjustable by sliding the first portion through the sliding structure.

In a method of anchoring a transcatheter valve prosthesis in a cardiovascular structure for replacing a native valve, the transcatheter valve prosthesis may include an expandable stent having a plurality of individually expandable cells. The method may include introducing into the cardiovascular structure a first delivery device having an anchoring device therein in a contracted configuration. The anchoring device may include an expandable ring having a central axis extending in a longitudinal direction, a support structure extending from the expandable ring in the longitudinal direction, and at least one anchor coupled to the support structure and extending radially inwardly from the support structure. The method may also include guiding the first delivery device to a deployment location downstream of the native valve. Additionally, the method may include deploying the anchoring device from the first delivery device such that the at least one anchor is positioned within a sinus of the native valve. Further, the method may include guiding a second delivery device containing the transcatheter valve prosthesis to the native valve, and deploying the transcatheter valve prosthesis from the second delivery device within the native valve such that a portion of a leaflet of the native valve is pinched between the at least one anchor and the transcatheter valve prosthesis.

In a further aspect of the present disclosure, a method of positioning an anchoring device within a cardiovascular structure may include introducing into the cardiovascular structure a delivery device having an anchoring device therein in a contracted configuration. The anchoring device may include an expandable ring having a central axis extending in a longitudinal direction, a support structure extending from the ring in the longitudinal direction, and at least one anchor coupled to the support structure and extending radially inwardly from the support structure. The method may also include guiding the delivery device to a deployment location downstream of a native valve. Additionally, the method may include deploying the anchoring device from the delivery device such that the at least one anchor is positioned within a sinus of the native valve.

These and other embodiments of the present disclosure are more fully described herein below.

BRIEF DESCRIPTION OF THE DRAWINGS

The features, aspects, and advantages of the present invention will become better understood with regard to the following description, appended claims, and accompanying drawings in which:

FIG. 12 is a perspective view of a second embodiment of a stud-type anchoring device.

FIG. 13 is a perspective view of a third embodiment of a stud-type anchoring device.

FIG. 14 is a perspective view of a fourth embodiment of a stud-type anchoring device.

FIG. 15 is a perspective view of a fifth embodiment of a stud-type anchoring device.

DETAILED DESCRIPTION

Figure 1A:
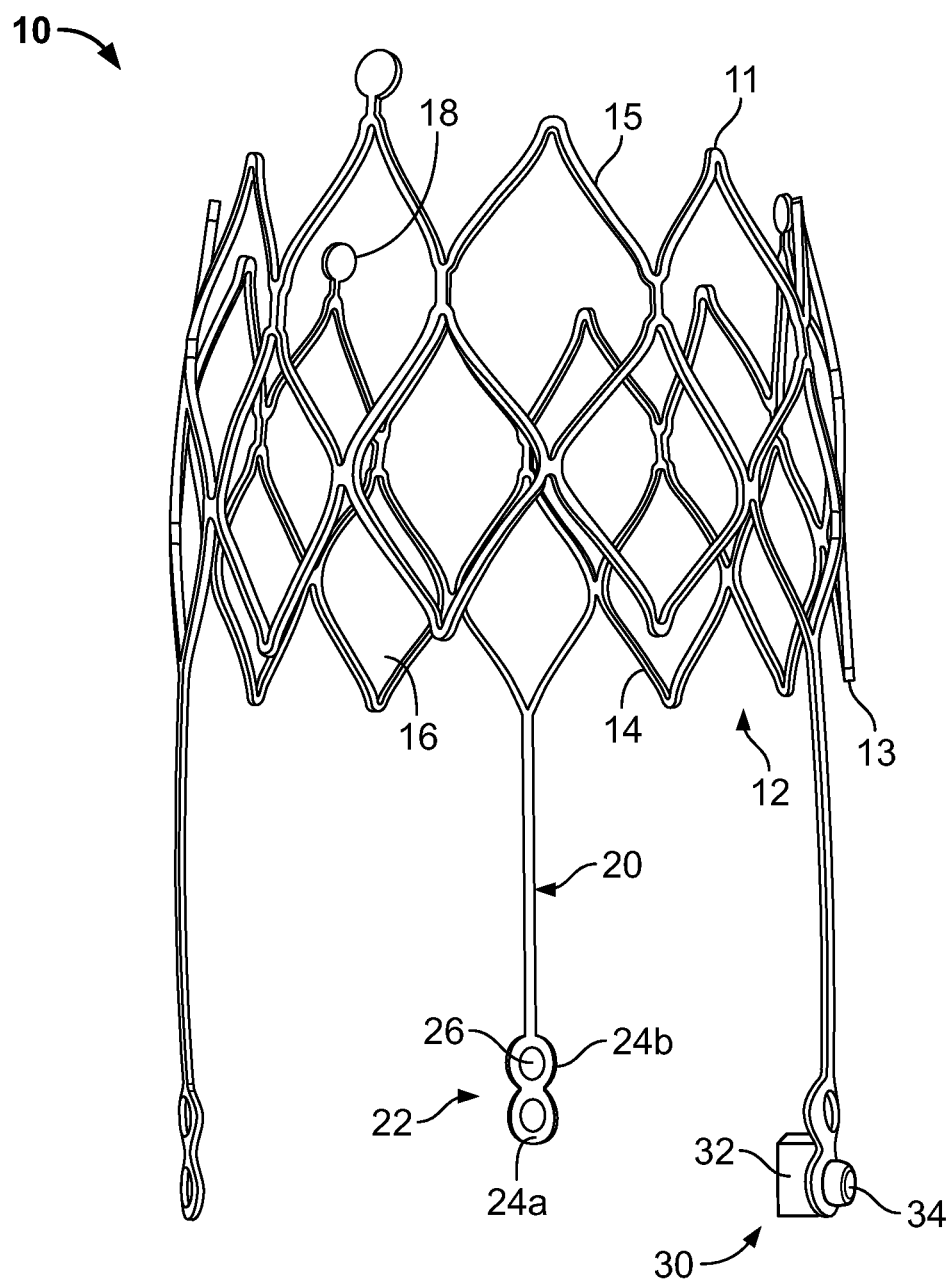
FIG. 1A is a front perspective view of one embodiment of an expandable anchoring device including legs, attachment portions, and an anchor.
Figure 1B:
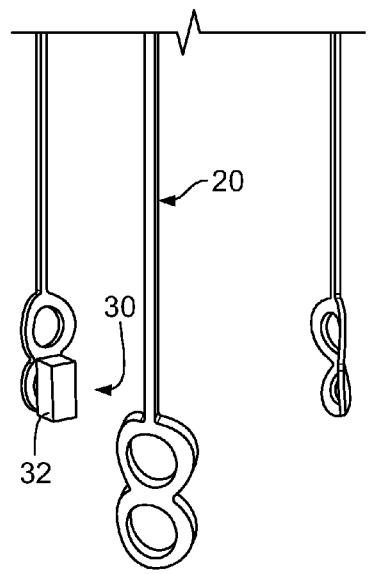
FIG. 1B is a rear partial perspective view of the anchoring support and anchor of FIG. 1A.
Figure 1C:
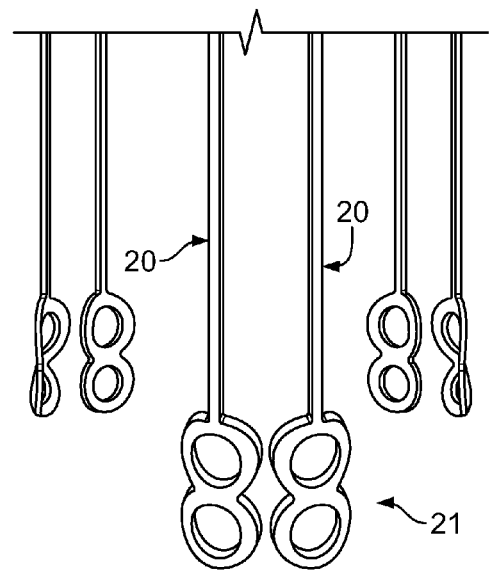
FIG. 1C is a partial perspective view the legs grouped in three leg bundles of two legs per bundle.

Multiple valves exist in the cardiovascular system of the human body including the heart and veins. While the following discussion specifically refers to the use of anchoring devices in procedures involving the aortic valve, it is to be understood that the anchoring devices described herein may be utilized in connection with procedures involving other valves including, but not limited to, bicuspid and tricuspid cardiac valves, including the mitral valve.

Further, it is to be understood that the anchoring devices disclosed herein may be utilized in conjunction with any stented transcatheter device, for example, Portico® transcatheter aortic valves (St. Jude Medical, Inc., St. Paul, Minn.). Additionally, such anchoring devices may accommodate a transcatheter valve prosthesis delivered via any delivery approach including, but not limited to, transfemoral, transapical, transaortic, transseptal and subclavian approaches.

When used in connection with devices for delivering an anchoring device into a patient, the terms "trailing" and "leading" are to be taken as relative to the user of the delivery device. "Trailing" is to be understood as relatively close to the user, and "leading" is to be understood as relatively farther away from the user). Additionally, the term "vascular structure" as used herein can be any cardiovascular structure including a coronary annular and/or valvular structure. Also, as used herein, the terms "about," "generally" and "substantially" are intended to mean that slight deviations from absolute are included within the scope of the term so modified.

Transcatheter valve prostheses commonly include a stent body comprised of struts forming individual cells. An artificial valve assembly typically constructed of bioprosthetic tissue, such as porcine or bovine tissue, is generally sewn to the stent body. When implanted into a vascular structure, there is a possibility that transcatheter valve prostheses may migrate. Such migration may be prohibited by calcium deposits or plaque formed on the native valve leaflets, which provide natural anchoring points. However, many patients with valvular insufficiency have insufficient calcification or other deposits to provide anchoring support. The present disclosure presents various embodiments of artificial anchoring structures that may be utilized where natural anchoring structures do not exist or are insufficient.

Artificial anchoring devices, as exemplified by the embodiments disclosed herein, can be constructed to have any number of structures capable of being deposited within the cardiovascular system. One general example is a structure that is capable of being expanded to generally conform to the vascular structure. Another example is a structure capable of penetrating the vascular structure, which anchors the anchoring device firmly in place.

FIGS. 1A-1D depict a first embodiment of an expandable anchoring device for use within a vascular structure. The anchoring device 10 may be utilized to provide a solid anchoring platform for a transcatheter valve prosthesis in order to prevent valve migration, as discussed further below. The anchoring device 10, as shown, includes an expandable body 12, retaining tabs 18, legs 20, attachment portions 22, and an anchor 30.

The expandable body 12, retaining tabs 18, legs 20, and attachment portions 22 may be made from any biocompatible material including, but not limited to, stainless steel, nickel-titanium alloy (commonly referred to as "Nitinol"), titanium, cobalt-chromium and biocompatible polymers. One or more components or features of anchoring device 10 may be made from or include a radiopaque material.

Additionally, the anchor 30 may be made from pyrolytic carbon, polyethylene glycol ("PEG"), polyethylene ("PE"), nylon, thermosensitive polymeric hydrogel, light-responsive hydrogel, or other environmentally sensitive hydrogels, other biocompatible polymers, Nitinol, Nitinol expandable foam, stainless steel, cobalt chromium, and other biocompatible metals, for example. Further, the anchor 30 may be coated with a radiopaque material or include radiopaque fillers.

The expandable body 12 is can be an annular stent comprised of a plurality of struts 14 forming individual expandable cells 16. The stent has a stent end 11, a leg end 13 and an expandable passageway 15 extending therethrough. The expandable cells 16 can be arranged in a double row pattern as shown, or may be arranged in a multitude of other patterns, for example, a single or triple row pattern. Additionally, when the expandable body 12 is a stent, the stent may be configured to allow the anchoring device to be unsheathed from and resheathed within a delivery device in order to provide the operator the ability to reposition the anchoring device in vivo.

The expandable body 12 may have an annular section with a first cross-section that flares outwardly to a flared section such that the annular section has a smaller cross-sectional area than the flared section when in an expanded state. Alternatively, the expandable body 12 may be a thin rounded or flattened wire-like structure that is collapsible into an accordion-like configuration and expandable into a planar ring shape or a ring that maintains bends along its circumference when expanded in order to facilitate collapsibility. A nonmetallic cuff may be attached to the inside diameter of the expandable body 12. The nonmetallic cuff may help limit or prevent metal-to-metal contact when fully implanted in conjunction with a transcatheter valve prosthesis that extends into the passageway 15 of the body 12. In some embodiments, the expandable body 12 may be about 2 mm to about 40 mm in length measured from the stent end 11 to the leg end 13.

The expandable body 12 may optionally include one or more retaining tabs 18 at the stent end thereof. The retaining tabs 18 may be sized and shaped to cooperate with corresponding retaining features provided within a delivery device, as further described below.

The anchoring device 10 includes at least one leg 20 extending from the leg end 13 of the expandable body 12. In some embodiments, the anchoring device 10 may include a plurality of legs 20, for example, the anchoring device 10 may have about 1 to 9 legs 20. Preferably, the anchoring device 10 includes at least one leg 20 per valve leaflet. As an example, when anchoring is to occur at an aortic valve, an anchoring device 10 may be selected having three legs 20 spaced apart such that the first leg corresponds with the right semilunar cusp, the second leg corresponds with the left semilunar cusp, and the third leg corresponds with the posterior semilunar cusp.

Figure 1D:
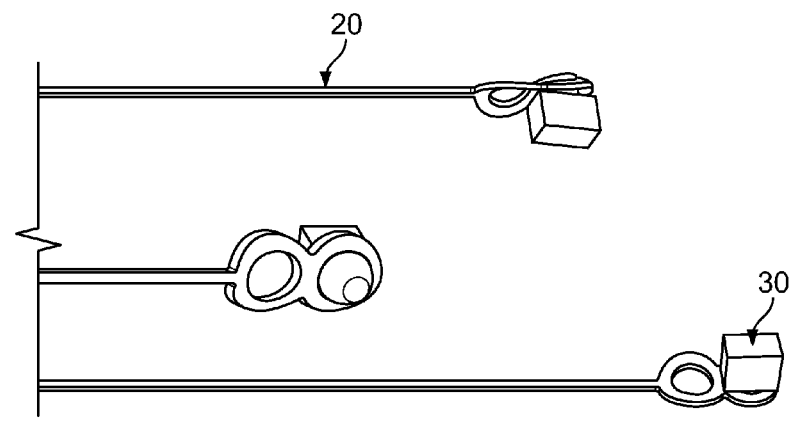
FIG. 1D is a partial perspective view of the legs of FIG. 1A varying in length and each including an anchor.

In another example, the anchoring device 10 may include bundles 21 of two or more legs 20 per valve leaflet, as depicted in FIG. 1D. As an example, the anchoring device 10 may include three pairs of legs 20, or six legs total, such that each pair of legs 20 corresponds to one valve leaflet. In yet a further example, the anchoring device 10 may include three groups of three legs 20, or nine legs total, such that each group of three legs 20 corresponds to one valve leaflet. Similarly, where the target valve is a bicuspid valve, the anchoring device 10 may have two legs 20, two pairs of legs 20, or two groups of three legs 20, for example.

All of the legs 20 in a single anchoring device 10 may have the same length, as shown in FIG. 1A, or the lengths of the legs 20 in a single device may differ. FIG. 1D illustrates legs 20 with different lengths, with each leg 20 including an anchor 30. The different lengths of the legs 20 may position the anchor 30 of each leg 20 in a different longitudinal location in order to avoid interfering with one another during the crimping process, which may allow the anchoring device 10 to be placed in a smaller diameter delivery device. Additionally, positioning the anchor 30 of each leg 20 in a different longitudinal location, rather than positioning all of the anchors 30 in a single plane, may increase the probability of an anchor 30 catching a strut of a transcatheter valve for valve anchoring.

In some embodiments, the length of each leg 20 may be different from the lengths of the other legs, as exemplified in FIG. 1D. In other embodiments, some of the legs 20 may have the same length, while other legs may have a different length. For example, first and second legs may have the same length, which may be different from that of a third leg. In other embodiments in which the legs 20 are grouped into two or more bundles, each corresponding to a valve leaflet, each leg in a bundle may have a different length, yet a leg in one bundle may be equal in length to a leg in another bundle. For example, where the target valve is a tricuspid valve and an anchoring device is selected to have three groups of three legs each, the three legs in each individual group may have different lengths, but the first leg of each group may all have the same length, the second leg of each group may all have the same length, and the third leg of each group may all have the same length.

Whether the legs 20 are all equal in length or of different lengths, the length of each leg 20 can be characterized as long or short. Short legs are defined herein as those allowing the transcatheter valve to at least partially extend into the passageway 15 of the expandable body 12 when fully implanted and anchored by the anchoring device 10 in vivo. Long legs are defined herein as those allowing the expandable body 12 to extend out of reach of the transcatheter valve such that an implanted and anchored transcatheter valve prosthesis does not extend into the passageway 15 of the body 12. In some embodiments, the legs 20 can be about 2 mm to about 60 mm in length as measured from the connection with the body 12 to the connection with the anchor 30 or attachment portion 22. Preferably, the legs 20 have enough length to place the expandable body 12 downstream of the openings of the coronary arteries, such as at the sinotubular junction, and are thin enough to not obstruct blood flow into the coronary arteries in the event a leg 20 is placed over a coronary artery opening.

The attachment portions 22 extend from each leg 20. As shown in FIGS. 1A-1D, each attachment portion 22 includes a first support 24a and a second support 24b. Each support 24a, 24b includes an eyelet 26 extending therethrough. Additionally, each support 24a, 24b may have curved or rounded edges to reduce or eliminate irritation and/or potential damage to the vascular structure when implanted and during deployment. Further, the attachment portion 22 may have a curvature configured to conform to the curvature of the vascular structure.

The eyelets 26 and supports 24a, 24b are sized to receive, retain, and support at least one anchor 30. Additionally, the first and second supports 24a, 24b and respective eyelets 26 may be spaced along their respective leg 20 to allow for more than one anchor 30 to be attached to each leg 20, and in some embodiments, to allow for a space between each attached anchor 30.

The anchor 30 is depicted as a rivet-like device that includes a body 32 and a head 34. The head 34 may be sized to extend through either the first or second eyelet 26 and may be subsequently deformed, such as by heat or mechanical force, so that it cannot be pulled out from the eyelet 26 and removed from the support. In some embodiments, the anchor may be connected to the attachment portion 22 by forming the body 32 and head 34 separately and connecting them together through an eyelet 26 by mechanical means, such as by press-fit or threaded fixation. In other embodiments, anchors 30 and legs 20 may be formed together as a monolithic structure. As these are merely examples, it is envisioned that a person having ordinary skill in the art could couple legs 20 to anchors 30 in any number of different ways without departing from the spirit and scope of the present invention.

The body 32 of anchor 30 is illustrated as being a rectangular prism. However, the body 32 can have any shape including, but not limited to, spherical, triangular prismatic, oval, and polygonal shapes, for example. Additionally, the surfaces of the body 32 may be polymer coated, textured and/or include notches etched into these surfaces to mimic the peaks, valleys and contours of natural calcium and plaque deposits. In one embodiment, the anchor may be constructed from a hydrogel that can be activated to expand in volume upon the application of a stimulus, such as heat or light, for example. When the anchor is constructed from such hydrogel, the hydrogel may be attached to the supports in globules and may be attached by sewing or molding around the support structure, for example. The hydrogel construction may allow for the globules to be smaller than a fixed size anchor to allow anchoring device 10 to be loaded into a smaller diameter delivery device. In such embodiments, the expandable body 12 may be configured to transfer heat to the hydrogel globules so that activation temperature can be reached.

The expandable body 12, legs 20, retaining tabs 18, and attachment portions 22 may be laser cut from a tube or otherwise constructed from a single piece of material so as to form a monolithic anchoring device structure. However, in some embodiments, any one of these structures may be separately formed and connected to the other structures by mechanical means, such as welding or bonding.

As the retaining tabs 18, legs 20, and attachment portions 22 are each directly or indirectly coupled to the expandable body 12, each of these structures may move in unison with the expandable body 12 when the body is collapsed or expanded. However, the legs 20 may be naturally biased toward radial expansion separate and apart from the expansion of the expandable body 12 such that when the legs 20 are unsheathed from a delivery device prior to the body 12, the legs 20 flare outward toward the vascular structure. This independent expansion allows the operator to more accurately determine the positioning of the anchor 30 during deployment.

One aspect of the present disclosure includes methods of anchoring a stented device, such as anchoring a transcatheter valve prosthesis in a native valve annulus. Generally, such methods include guiding a delivery device containing anchoring device 10 to a location downstream of the target valve and deploying the anchoring device 10 such that at least one anchor 30 is placed within a sinus of the target valve between the valve leaflets and vascular wall. A transcatheter valve prosthesis may then be guided to the target valve and deployed such that the native valve leaflets are pinched between the stent of the transcatheter valve and the anchor 30.

Figure 2A:
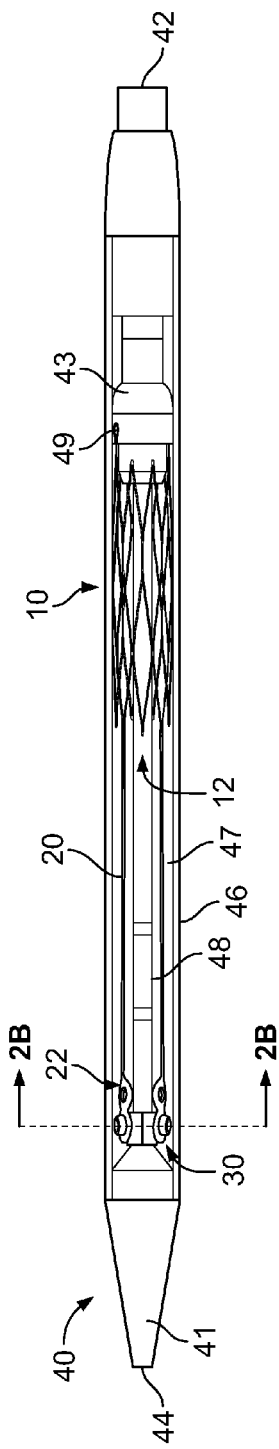
FIG. 2A is a cutaway view of a delivery device containing the anchoring device of FIG. 1A with an anchor attached to each attachment portion.

FIG. 2A depicts a delivery device 40 loaded with an anchoring device 10 having an anchor 30 attached to an attachment portion 22. Examples of delivery devices and systems that may be utilized in conjunction with anchoring device 10 are described in U.S. Publication No. 2012/0053681, the entirety of which is hereby incorporated herein by reference. The delivery device 40 has a trailing end 42 and a leading end 44, and generally includes an inner shaft 48 surrounded by a retractable sheath 46. An atraumatic tip 41 may be affixed to the leading end 44 of the inner shaft 48 and may be configured to enclose the open end of sheath 46 when the sheath is in a fully extended position. A retainer 43 may be affixed to inner shaft 48 at a spaced distance from atraumatic tip 41, thereby defining a compartment 47 between retainer 43 and tip 41 for receiving anchoring device 10. Retainer 43 may optionally include recesses 49 for receiving retaining tabs 18 when anchoring device 10 is assembled in compartment 47. The delivery device 40 may be preloaded with an anchoring device 10 during the manufacturing process and delivered to the surgical site in the preloaded condition, or, alternatively, the delivery device 40 may be loaded with an anchoring device 10 at the surgical site.

The delivery device 40 is loaded by crimping anchoring device 10 and placing it within compartment 47 such that the inner shaft 48 passes through the passageway 15 of the expandable body 12. When anchoring device 10 includes retaining tabs 18, the retaining tabs 18 may be engaged in the recesses 49. The engagement of the retaining tabs 18 in the recesses 49 helps maintain the anchoring device 10 in an assembled relationship with the delivery device 40, minimizes longitudinal movement of the anchoring device relative to the delivery device during unsheathing or resheathing procedures, and helps prevent rotation of the anchoring device relative to the delivery device as the delivery device is advanced to the target location and during deployment.

Figure 2B:
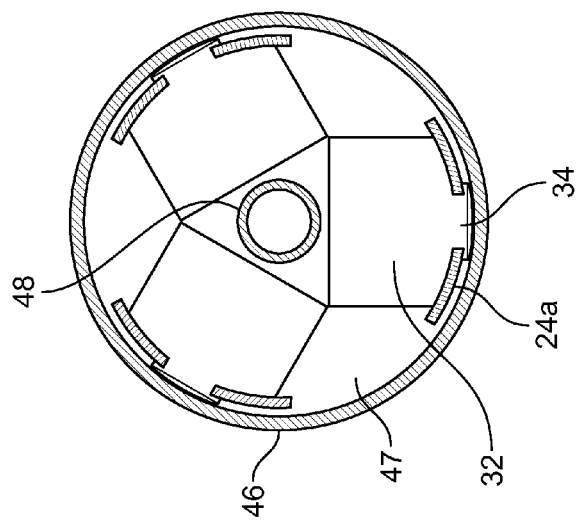
FIG. 2B is a cross-sectional view of the delivery device and anchoring device taken along line 2B-2B of FIG. 2A.

FIG. 2B is a cross-sectional view taken along line 2B-2B of the anchoring device 10 in a loaded configuration within the delivery device 40. The cross-sectional view shows anchor bodies 32 arranged in a symmetric radial pattern and abutting one another in the crimped state of anchoring device 10. In some embodiments, bodies 32 may be smaller in size, such as when bodies 32 are constructed of hydrogel, or have varying shapes such that bodies 32 each abut the inner shaft in the crimped state of anchoring device 10. In other embodiments, the bodies 32 may be staggered in a longitudinal direction of anchoring device 10, which may facilitate tighter crimping of the device. In further embodiments, the arrangement of the legs and anchoring bodies 32 may not be radially symmetric, particularly when it is determined that a particular region of the native target valve is in need of more anchoring support than another.

Figure 2C:
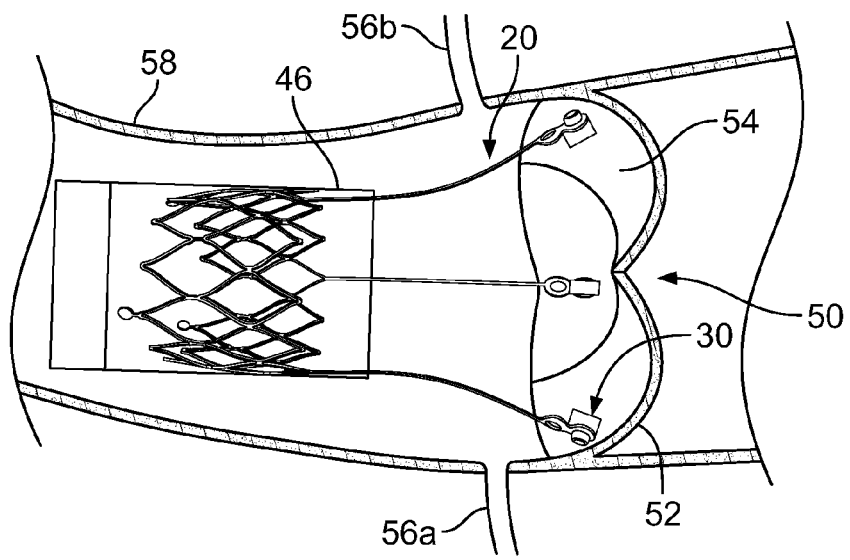
FIG. 2C is a schematic view of the anchoring device of FIG. 2A partially unsheathed within an aorta.

As depicted in FIG. 2C, the loaded delivery device may be guided under radiographic guidance and along a guidewire passing through the inner shaft 48 to a location downstream of the leaflets 52 of a target aortic valve 50. The anchoring device 10 may then be partially developed by retracting sheath 46. When the legs 20 are independently expandable, they may flare outwardly as they are deployed from the delivery device 40, which may facilitate accurate assessment of the positioning of the anchors 30 with respect to the native valve leaflets 52. Each anchor 30 is preferably positioned in a designated aortic sinus 54 between the leaflets 52 and wall 58 of the aorta. In instances in which it is determined the anchors 30 are out of position, the anchoring device 10 may be resheathed and repositioned.

Figure 2D:
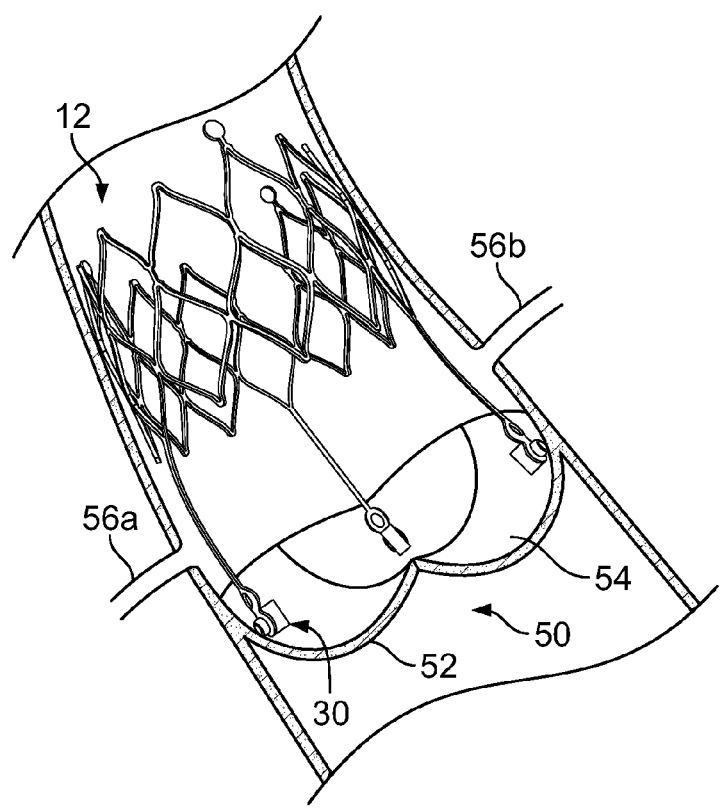
FIG. 2D is a schematic view of the anchoring device of FIG. 2A deployed within the aorta.

Once the anchors 30 are positioned in the desired locations within native valve sinuses 54, the deployment of anchoring device 10 may be completed, as depicted in FIG. 2D. Complete deployment may be achieved by fully retracting sheath 46 and allowing the anchoring device 10 to expand into a final position. When the anchoring device 10 is not self-expandable, deployment may be achieved by retracting sheath 46 and inflating a balloon disposed within the passageway 15 of the expandable body 12 to expand the anchoring device 10 into the final position. In the final position, the expandable body 12 preferably resides downstream of the openings of the left and right coronary arteries 56a, 56b and presses against the wall 58 of the aorta.

With regard to the multiple leg bundle embodiments described above, each bundle of legs may extend into a designated aortic valve sinus. Additionally, when each leg 20 in a bundle or each leg 20 of the anchoring device 10 has a different length, the leg lengths may fall within a range such that each anchor 30 is confined to a valve sinus 54 when fully implanted. Alternatively, leg lengths may differ such that at least one anchor 30 is positioned outside of a valve sinus 54 where it will directly contact the transcatheter valve. Care should be taken to avoid positioning an anchor 30 in front of an opening to a coronary artery 56a, 56b. Some leg configurations may be selected such that the legs 20 extending into the left and right aortic sinus extend farther into their respective sinuses than the leg or legs extending into the posterior aortic sinus in order to avoid positioning the anchors in front of the coronary arteries 56a, 56b.

In a transapical delivery, the delivery device (not shown) may be configured to unsheath toward the aortic arch, and, in some embodiments, toward the apex of the heart. In a transapical delivery approach where the delivery device is unsheathed toward the aortic arch, the legs 20 of anchoring device 10 may be oriented within the delivery device such that they are closer to the operator than the body 12, which is in contrast to a transfemoral approach where the legs are oriented in a position further from the operator than the body 12. The delivery device may be guided through the left ventricle and through the aortic valve such that anchoring device 10 is positioned within the aorta downstream of the aortic valve. Thereafter, the anchoring device is at least partially unsheathed. As the delivery device is partially unsheathed the legs 20 may expand outward and be in a position for placement within the aortic sinuses. With the anchors 30 partially unsheathed and properly aligned with the valve leaflets 52, the operator may then pull the delivery device toward the left ventricle to seat the anchors 30 within their designated aortic sinuses 54. The anchoring device 10 may then be fully deployed and the delivery device removed by pulling it through the expanded passageway 15 of the body 12.

Once the anchoring device 10 has been implanted, a transcatheter valve prosthesis (not shown) may be guided to the target valve 50 either using the same delivery device 40 or another delivery device and then fully deployed in an anchored arrangement with the valve leaflets 52 and anchors 30. Where the prosthetic valve is resheathable, the prosthetic valve may be partially deployed from the delivery device to assess for positional alignment and paravalvular leaks. If it is determined that the prosthetic valve is not properly positioned, it may be resheathed and repositioned prior to full deployment. In instances where a partially deployed prosthetic valve is resheathed from an anchored arrangement with the valve leaflets 52 and anchors 30, the positioning of the anchors 30 within respective aortic sinuses 54 behind the valve leaflets 52 helps prevent the prosthetic valve from being snagged by the anchors 30 as the valve is being resheathed, which helps reduce potential interference during resheathing of the valve while allowing for firm anchoring during full deployment of the valve.

An anchored arrangement generally includes the anchors 30 placed within designated aortic valve sinuses 54 between the valve leaflets 52 and aortic wall 58, and the valve leaflets 52 trapped between the anchors 30 and the stent of the prosthetic valve. This arrangement creates a pinching effect on the valve leaflets 52, which are naturally rooted to the underlying vascular structure. The pinching effect on the naturally rooted native valve leaflets 52 helps anchor both the anchoring device 10 and the prosthetic valve, preventing their migration.

As previously mentioned, the anchors 30 may take on multiple shapes and configurations to help simulate natural calcium and plaque build-up. In cases of severe stenosis, such natural calcium and plaque build-up typically anchor a transcatheter valve by providing an abutment surface that is firmly anchored to the naturally rooted valve leaflets or vascular structure. This abutment surface generally projects at least partially into an adjacent stent cell of the implanted transcatheter valve and abuts corresponding struts of the stent to restrict migration of the implanted valve. Similar to natural calcium or plaque build-up on the native leaflets 52, each anchor 30 may push a portion of a native leaflet 52 into an adjacent cell of the stent of the implanted valve, which provides an abutment surface naturally rooted to the native valve 50 and helps prohibit migration of the valve prosthesis.

Another benefit of the pinching effect is the potential reduction of paravavlular leaks. When an anchor 30 pushes a native valve leaflet 52 into or against the stent of a prosthetic valve, the native valve leaflet 52 helps provide a barrier to paravalvular leaks at that location. The use of anchors 30 in this manner may pull the valve leaflet tissue tight around 52 around the diameter of the transcatheter valve stent, which may help further seal off potential paravalvular leaks.

Figure 3A:
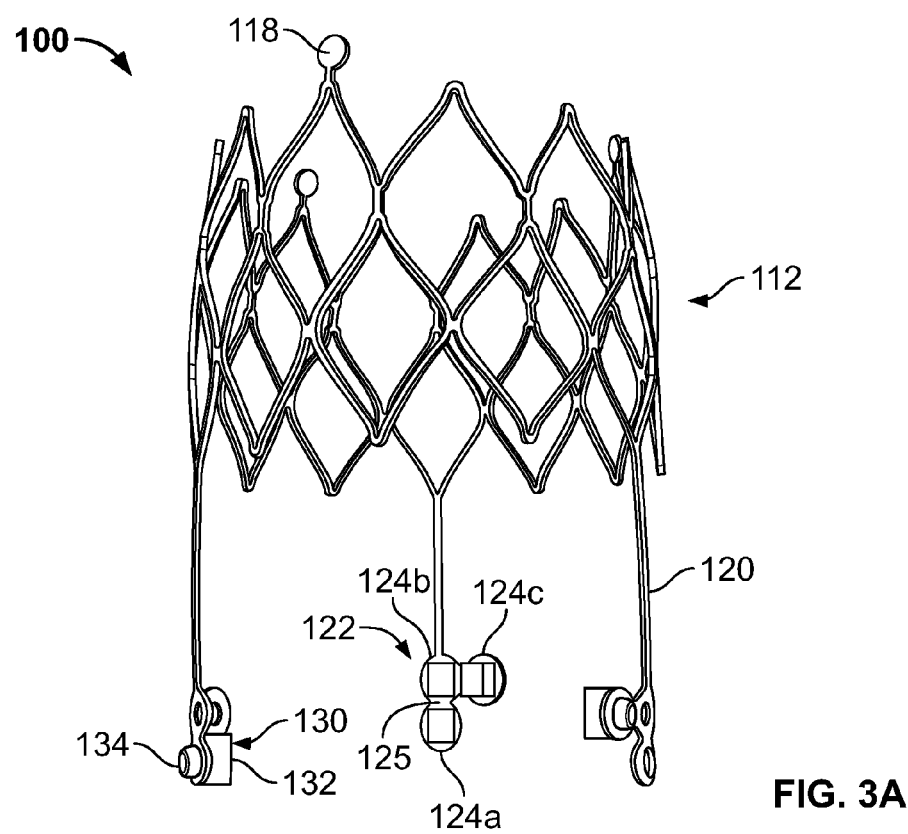
FIG. 3A is a front perspective view of another embodiment of an expandable anchoring device having alternative attachment portion and anchor configurations.

FIG. 3A depicts an alternative expandable anchoring device 100. Anchoring device 100 includes an annular expandable body 112 and legs 120 similar to those of anchoring device 10, but differs with respect to the attachment portions. Anchoring device 100 includes attachment portions 122 which each include a first, second, and third support 124*a-c*. The supports 124*a-c* are arranged in an upside-down L-shaped configuration in which the first support 124*a* and second support 124*b* are aligned collinearly with a leg 120, similar to the first support 24*a* and second support 24*b* of anchoring device 10. The third support 124*c* provides an additional anchor 130 attachment position and extends substantially orthogonally from the second support 124*b*. In variants hereof, the third support 124*c* may extend from the second support at any number of different angles.

Figure 3B:
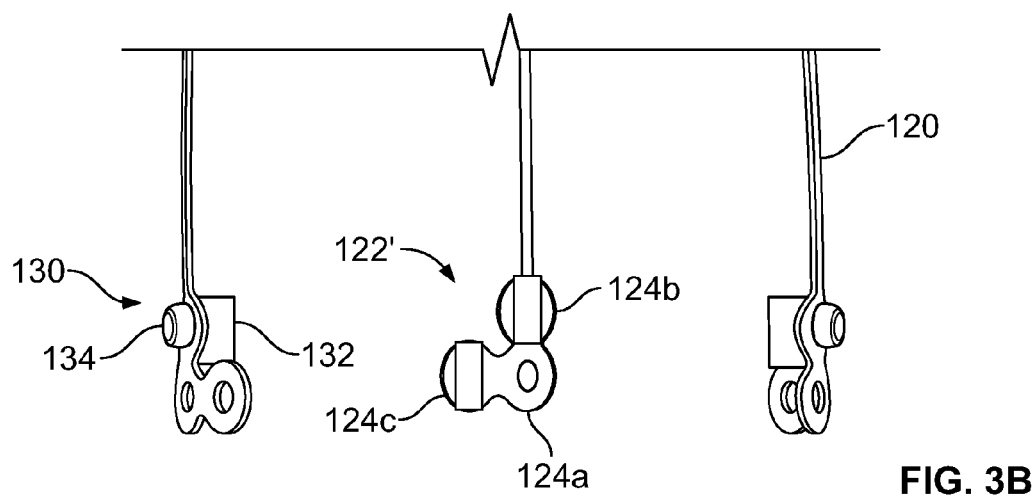
FIGS. 3B-3D are partial front views of alternative attachment portion and anchor configurations.
Figure 3C:
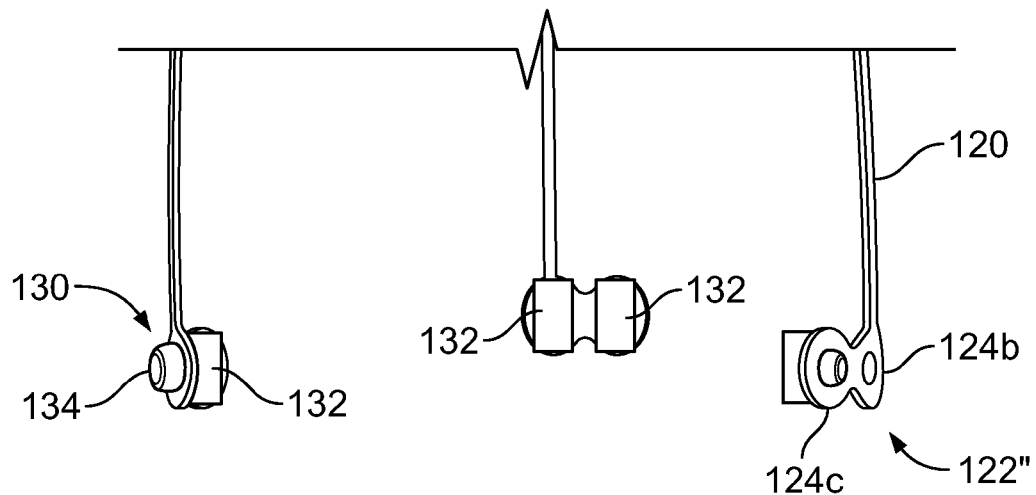

FIGS. 3B-3C illustrate other examples of attachment portion configurations. For instance, FIG. 3B illustrates attachment portions 122' having a right-side-up L-shaped configuration similar to that of FIG. 3A, but differing in the location of the third support 124*c*, which extends from the first support 124*a*. In another example, FIG. 3C illustrates attachment portions 122" similar to those of FIG. 3A, but eliminating first support 124*a* so that only the second support 124*b* and third support 124*c* remain.

Figure 3D:
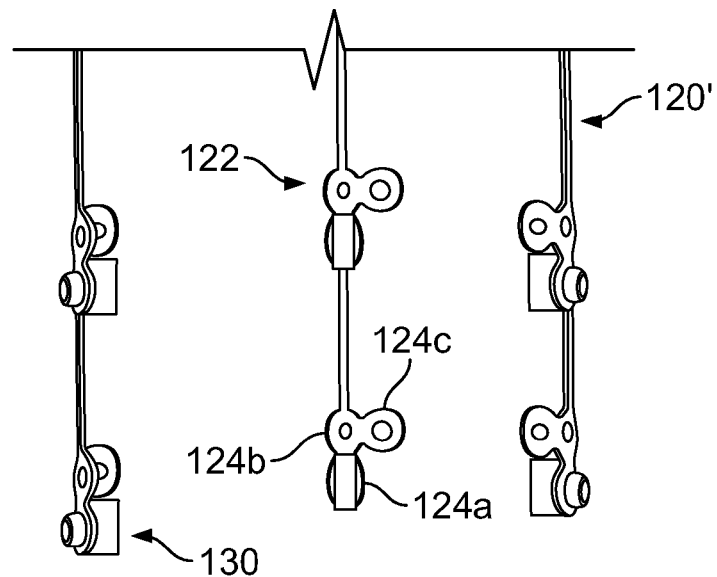

Each leg 120 can have several attachment portions stacked along its length, with the attachment portions capable of having multiple supports arranged in a variety of configurations. For example, FIG. 3D illustrates multiple ones of the attachment portion 122 of FIG. 3A stacked along leg 120'. Such a stacked configuration may increase the number of anchors 130 placed within a valve sinus and may also provide the operator added flexibility in positioning anchors 130 to more closely mimic the natural peaks, valleys, and contours of natural calcium and plaque deposits.

In addition to the numerous configurations of attachment portions, FIGS. 3A-3D illustrate various anchor configurations. For example, an anchor 130 may be attached to each support 124*a-c* of an attachment portion 122 and each support 124*a-c* may be spatially arranged so that there is a substantial space 125 between adjacent anchors 130 on an attachment portion. In another example, the anchors 130 may be attached to an attachment portion 122' such that more than one support but less than all the supports include an anchor. In a further example, the anchors may be attached to an attachment portion 122" such that only one support includes an anchor.

Any attachment portion and anchor configuration can be selected based on the patient's anatomy, the stent configuration of the transcatheter valve prosthesis, and/or the delivery device being utilized. While many other possible configurations have not be illustrated herein, it is to be understood that any combination of configurations previously described may be utilized and that many combinations and arrangements not exemplified herein may be utilized without departing from the inventive concept.

Figure 4A:
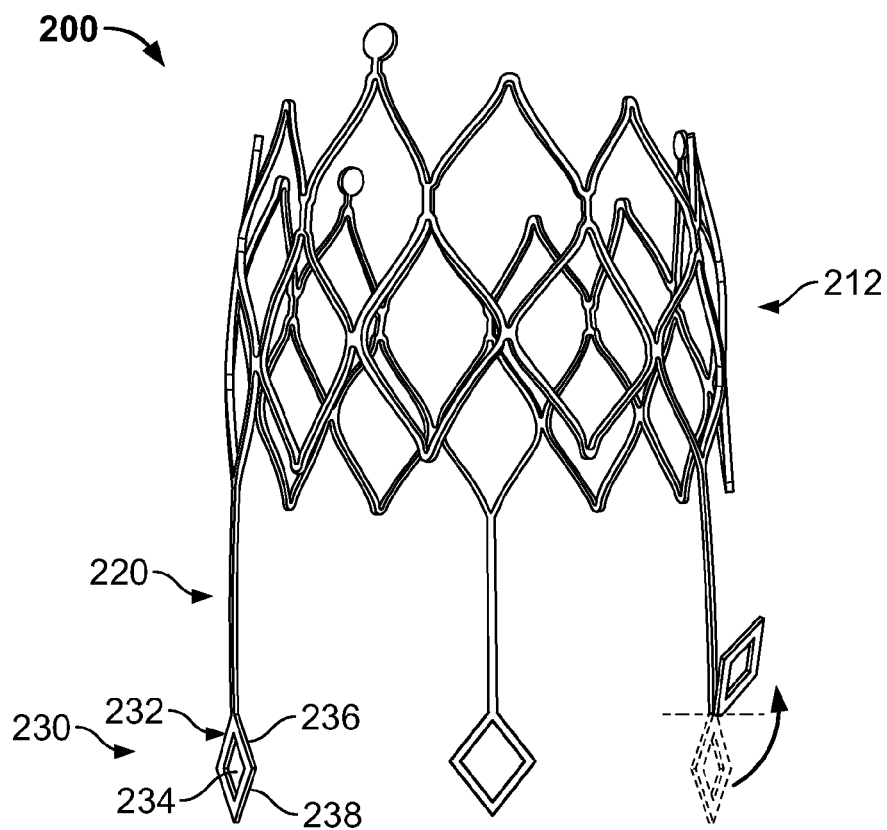
FIGS. 4A-4E are front perspective views of alternative embodiments of an expandable anchoring device having alternative anchor configurations.

While some anchoring devices can include various attachment portions and anchor configurations, other anchoring devices may not utilize an attachment portion and may directly connect the anchor to the leg. FIG. 4A illustrates an anchoring device 200 which exemplifies this concept. Anchoring device 200 includes an annular expandable body 212 and legs 220 similar to those of anchoring device 10, but differs with respect to the anchors. Anchoring device 200 includes anchors 230 that are each integrated into an leg 220 such that each leg 220 and its associated anchor 230 form a monolithic structure.

As shown, each anchor 230 has a diamond-shaped frame 232 with an aperture 234 defining a diverging portion 236 and a converging portion 238. The centers of the diverging portion 236 and the converging portion 238 lie on a longitudinal axis of the frame 232. The diverging portion 236 is joined to the converging portion 238 along an axis 237 that is substantially orthogonal to the longitudinal axis. The legs 220 and diamond-shaped frames 232 may be constructed from a memory metal, such as Nitinol, such that the frames 232 may bend along axis 237 from a first position to a second position upon the application of heat or mechanical force.

Figure 4B:
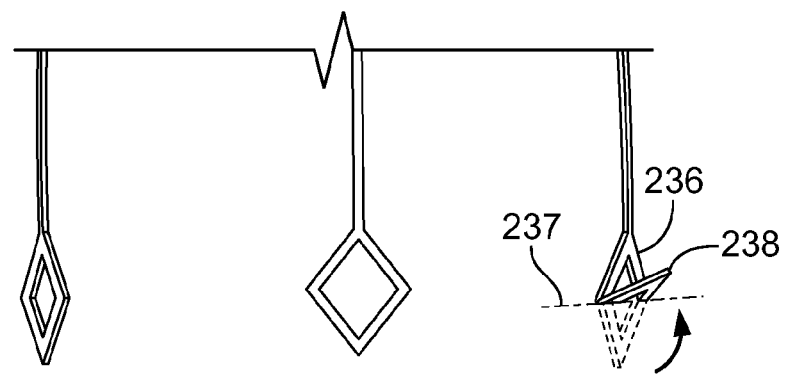

In the first position, the longitudinal axis of the frame 232 is substantially collinear with its associated leg 220, and the diverging portion 236 and converging portion 238 are substantially coplanar with one another and with leg 220. In the second position, the frame 232 may be bent radially inward or outward at its connection to leg 220, as shown in FIG. 4A. Alternatively, as illustrated by FIG. 4B, in the second position the converging portion 238 of the frame 232 may be bent along axis 237 radially inward or outward relative to diverging portion 236.

The anchoring device 200 may be loaded into a delivery device with the frames 232 in the first position which provides a smaller crimped profile than the second position. As anchoring device 200 is unsheathed, the patient's body temperature may cause the diamond-shaped frames 232 to move into the second position for implantation. In the second position, the frames 232 may push against the vascular wall or the valve leaflets to provide, in conjunction with the prosthetic valve, the pinching effect on the native valve leaflets as previously described herein.

Figure 4C:
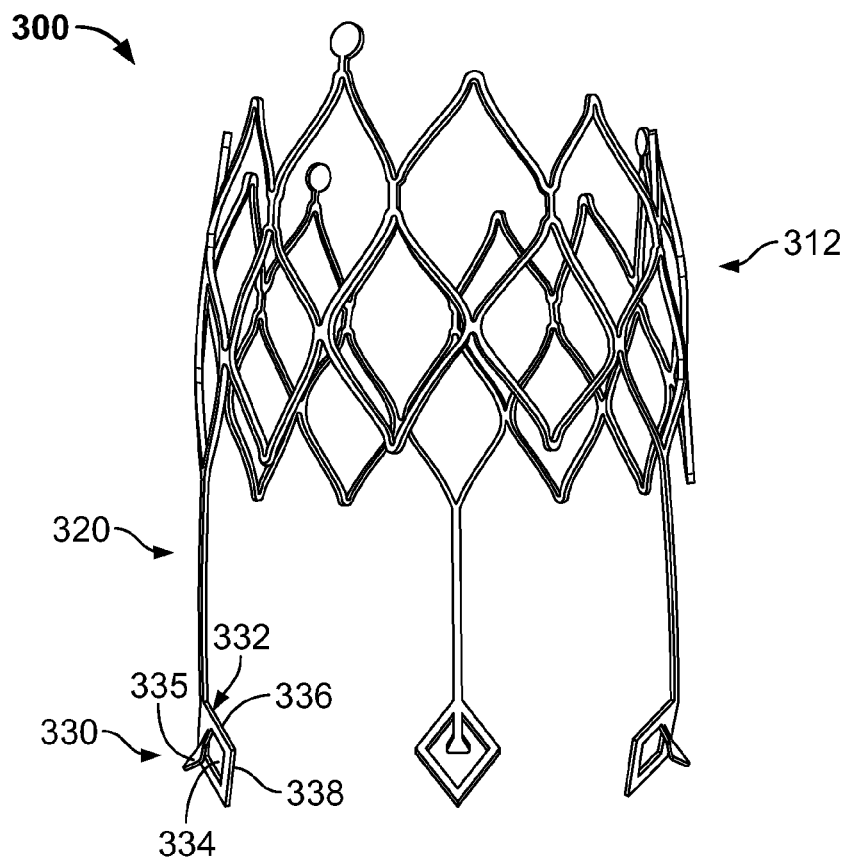
Figure 4D:
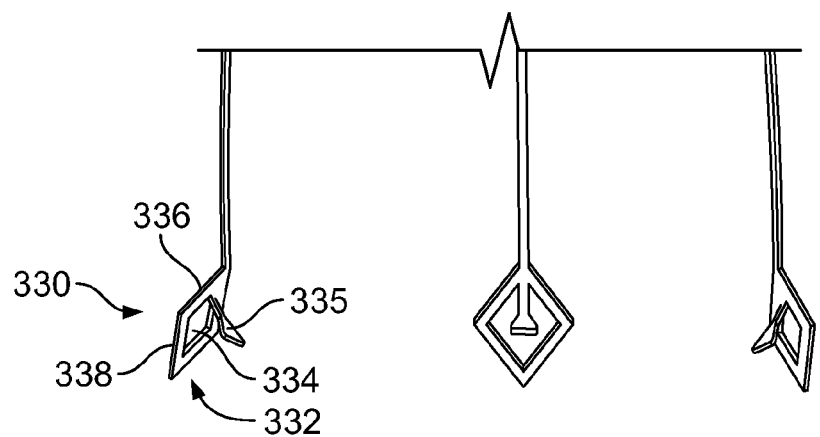

FIGS. 4C and 4D illustrate an alternative expandable anchoring device 300. Anchoring device 300 has an annular expandable body 312, legs 320, and anchors 330 similar to those of anchoring device 200 with the exception that the anchors 330 of anchoring device 300 include fingers 335 extending into the aperture 334 of the diamond-shaped frame 332. The fingers 335 may be bell shaped or any other shape that forms a broad tissue-contacting surface. Each finger 335 may extend from the center of the diverging portion 336 or converging portion 338 of the frame 332, but preferably extends from the diverging portion 336 in a direction away from body 312.

Similar to anchoring device 200, the anchors 330 may be moveable from a first position to a second position upon the application of heat or mechanical force. In the first position, the longitudinal axis of the frame 332 is substantially collinear with its associated leg 320 and with finger 335, and the diverging portion 336 and converging portion 338 are substantially coplanar with one another and with leg 320. In the second position, the frame 332 and finger 335 may be bent radially inward or outward at their connection to leg 320, and preferably, the finger 335 and frame 332 are bent in opposite directions relative to leg 320, as depicted in FIGS. 4C and 4D. Although not shown, the converging portion 338 of frame 332 may also be bent radially inward or outward relative to the diverging portion 336 in the second position, as described above in connection with anchoring device 200.

The first position may be beneficial for providing a small crimping profile for loading anchoring device 300 into a delivery device. During deployment, as the anchors 330 are unsheathed from the delivery device, the patient's body temperature may cause the anchors 330 to move from the first position to the second position. When anchoring device 300 is fully implanted, each finger 335 may press against the vascular wall and act as a support for its associated frame 332, which presses against a native valve leaflet to pinch the leaflet between the anchor 330 and a transcatheter valve prosthesis. Alternatively, each frame 332 may press against the vascular wall to support its associated finger 335, which presses against a native valve leaflet. In either case, the addition of the finger 335 to the frames 332 may provide additional stability and support for solid valve anchoring.

Figure 4E:
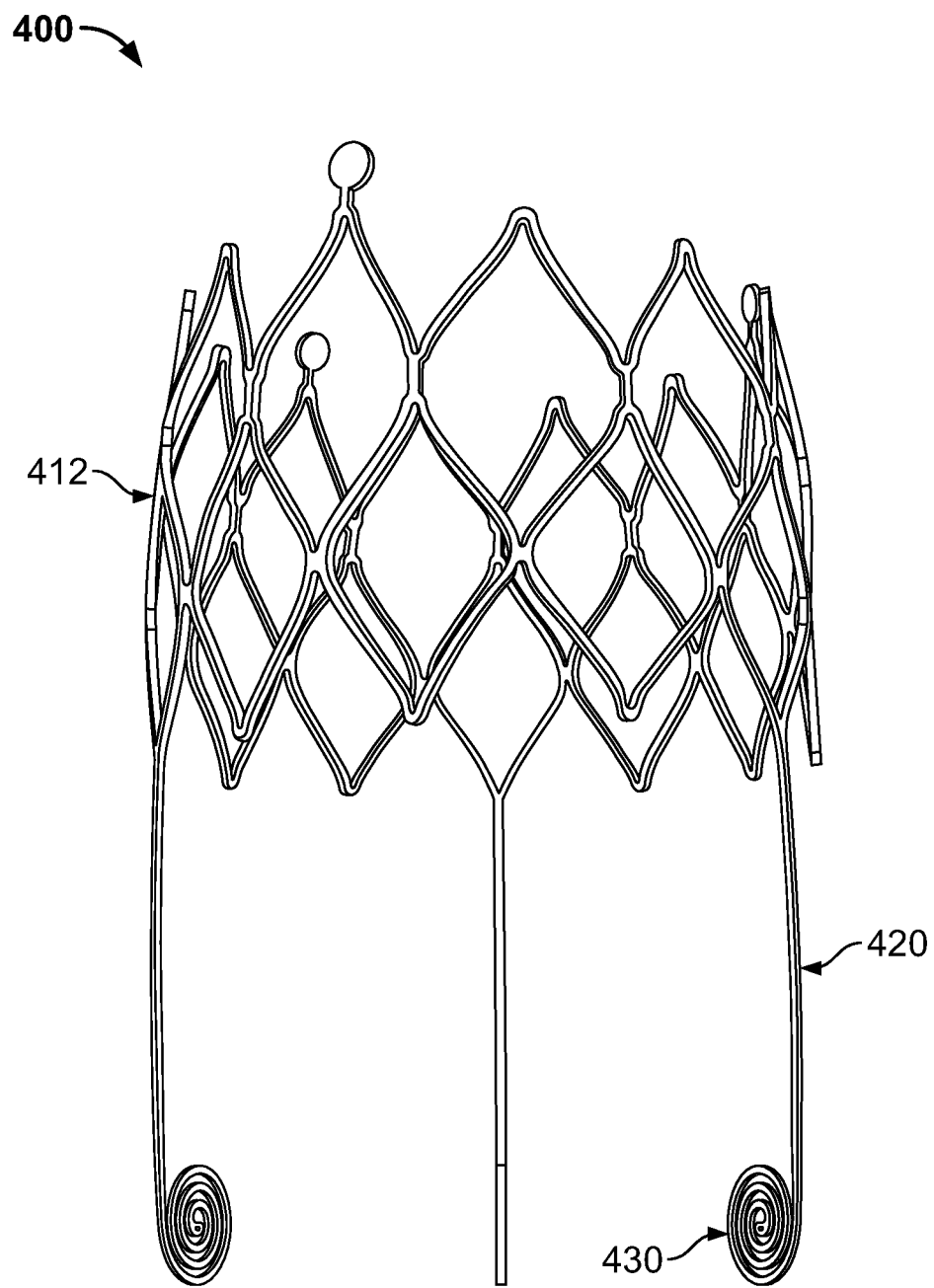

FIG. 4E depicts another expandable anchoring device 400. Anchoring device 400 includes an expandable annular body 412 and legs 420 similar to those of anchoring device 10, but differs with respect to the anchors. Anchoring device 400 includes coiled anchors 430 that are integrated into the free ends of legs 420 such that each leg 420 and a coiled anchors 430 form a monolithic structure. The coiled anchors 430 are coiled in a plane that is oriented in a radial direction relative to anchoring device 400 such that each coil projects radially inward from a corresponding leg 420.

Legs 420 and coiled anchors 430 may be constructed from a memory metal, such as Nitinol, such that the coiled anchors 430 are capable of moving from a first position to a second position upon exposure to heat or mechanical force. In the first position (not shown), the coiled anchors 430 are unraveled and appear as extensions of the legs 420. This may be beneficial for reducing the profile of anchoring device 400 for crimping and loading into a delivery device. The second position is as shown in FIG. 4E, with the anchors 430 fully coiled in radially inward directions.

During implantation, when anchoring device 400 is unsheathed from the delivery device, the exposure to the patient's body temperature may cause the free ends of the legs 420 to coil, thereby forming coiled anchors 430. When fully implanted, the coiled anchors 430 function similarly to anchors 30 by pinching one or more native valve leaflets between the transcatheter valve and one or more coiled anchors 430, thereby anchoring both anchoring device 400 and the transcatheter valve.

Figure 5:
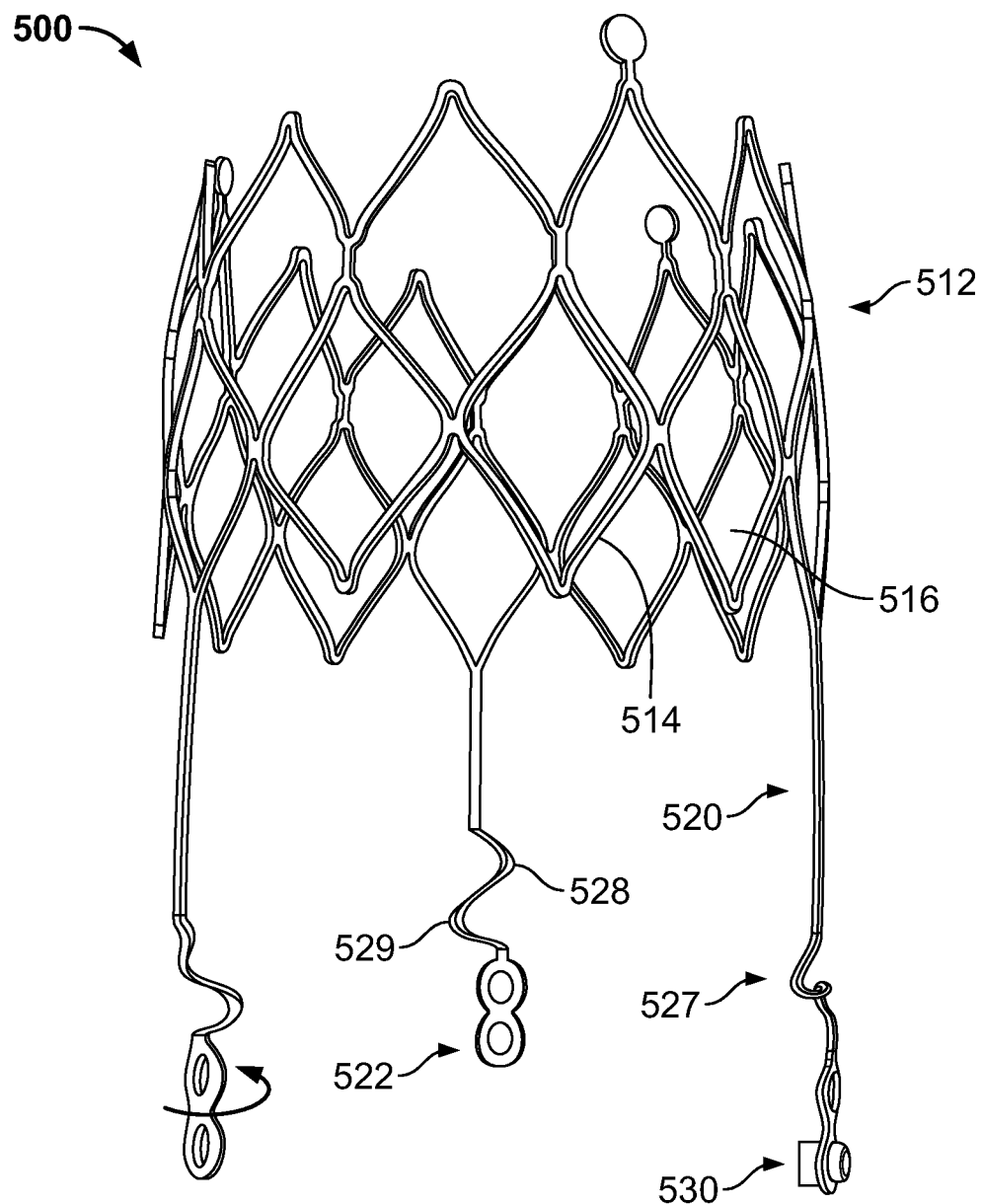
FIG. 5 is a front perspective view of yet another embodiment of an expandable anchoring device embodiment having an alternative configuration of the legs.

FIG. 5A depicts a further expandable anchoring device 500 having an annular expandable body 512, attachment portions 522 and anchors 530 similar to those of anchoring device 10, but having different legs. The legs 520 of anchoring device 500 include a tortuous or serpentine segment 527, which may be positioned adjacent each attachment portion 522. The tortuous segment 527 may include a first bend 528 and a second bend 529 that together form an S-shape. Additionally, the tortuous segment 527 may be twisted along its length from the first bend 528 to the second bend 529 such that the tortuous segment 527 is curved in three dimensions.

The tortuous segment 527 adds flexibility to the legs 520, which allows the attachment portions 522 to twist about an axis extending in a longitudinal direction of anchoring device 500, yet provides sufficient rigidity to limit or prohibit bending with respect to the longitudinal axis. The tortuous segments 527 may be constructed of a memory metal, such as Nitinol, so that they may move from a first condition to a second condition upon the application of heat or mechanical force. In one embodiment, each tortuous segment 527 may twist when exposed to an activation temperature so as to rotate a respective attachment portion 522.

In another embodiment, each tortuous segment 527 may twist by a predetermined amount when exposed to an activation temperature so as to rotate the respective attachment portion 522 by up to about 40 degrees. When implanted, the expansion of anchoring device 500 against the vascular wall may apply a torque to the tortuous segments 527 that increases the rotation of the attachment portions 522 up to about 90 degrees. This twisting feature allows the attachment portions 522, and any anchors 530 that may be attached thereto, to have a relatively small radial profile when crimped and loaded in a delivery device, and a relatively large radial profile when implanted. Further, the twisting action allows the attachment portions 522 to themselves function as anchors without an actual anchor 530 being attached thereto.

Figure 6:
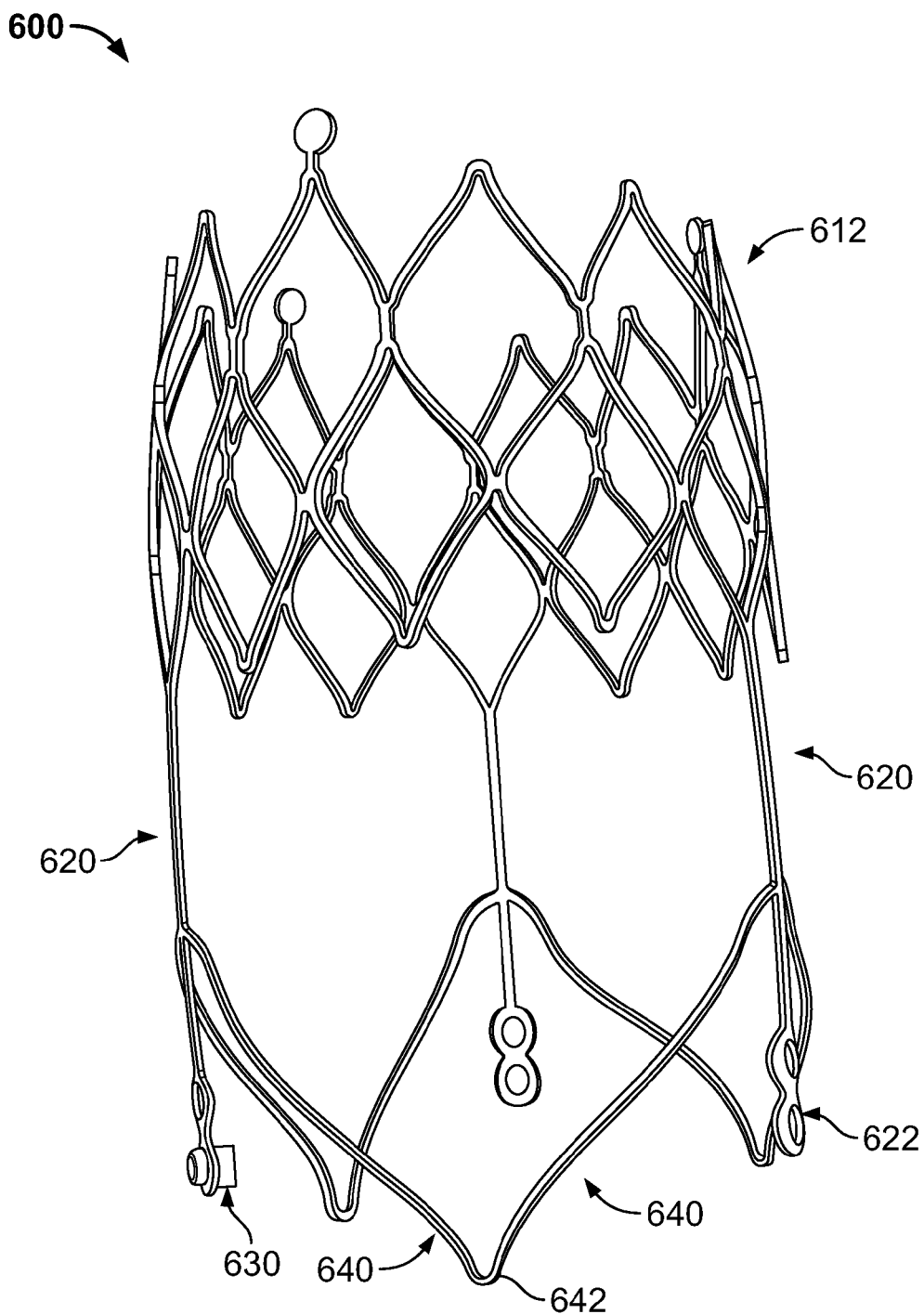
FIG. 6 is a front perspective view of a still further embodiment of an expandable anchoring device having expander arms.

FIG. 6 depicts yet another expandable anchoring device 600. Anchoring device 600 includes an annular expandable body 612, legs 620, attachment portions 622, and anchors 630 similar to those of anchoring device 10, but differs in that anchoring device 600 includes expander arms 640. Each leg 620 may have at least two expander arms 640 extending at an acute angle, preferably in a direction away from body 612, from a point along the length of the leg. Each expander arm 640 extending from one leg 620 joins an arm 640 extending from an adjacent leg 620 at an apex 642. Apices 642 are preferably positioned farther from the body 612 than the attachment portions 622 both when anchoring device 600 is in a crimped state and when it is in an expanded state. Preferably, anchoring device 600 includes the same number of apices 642 as there are leaflets in the native valve. The expander arms 640 may provide increased stability and support when anchoring device 600 is fully implanted. Additionally, the expander arms 640 may help the legs 620 remain in their expanded positions and assist in positioning anchoring device 600 in a desired orientation with respect to the target valve.

As device 600 is unsheathed during its deployment, the apices 642 of expander arms 640 are exposed first, followed by the legs 620. As the legs 620 begin to expand, the apices 642 remain farther from body 612 than the attachment portions 622, which allows the expander arms 640 to engage the target valve first. The apices 642 are each positioned in a designated valve sinus. The angle, which is typically an acute angle, formed by the intersection of expander arms 640 at the apices, helps center each apex 642 within its valve sinus. The centering of the apices 642 within the valve sinuses positions the attachment portions 622 and any attached anchors 630 within the commissure areas of the target valve. This allows the anchors 630 to directly engage the stent of the transcatheter valve for valve anchoring.

In some embodiments, globules of hydrogel (not shown) may be attached to the expander arms 640 at a location adjacent the apices for placement within the valve sinuses so that, when activated, they provide additional anchoring support by the pinching effect. In other embodiments, eyelets can be integrated with the arms at various locations along their respective lengths for anchor attachment. In still further embodiments, the apices 642 may be formed from or otherwise include radiopaque material for enhanced positional visualization.

Figure 7:
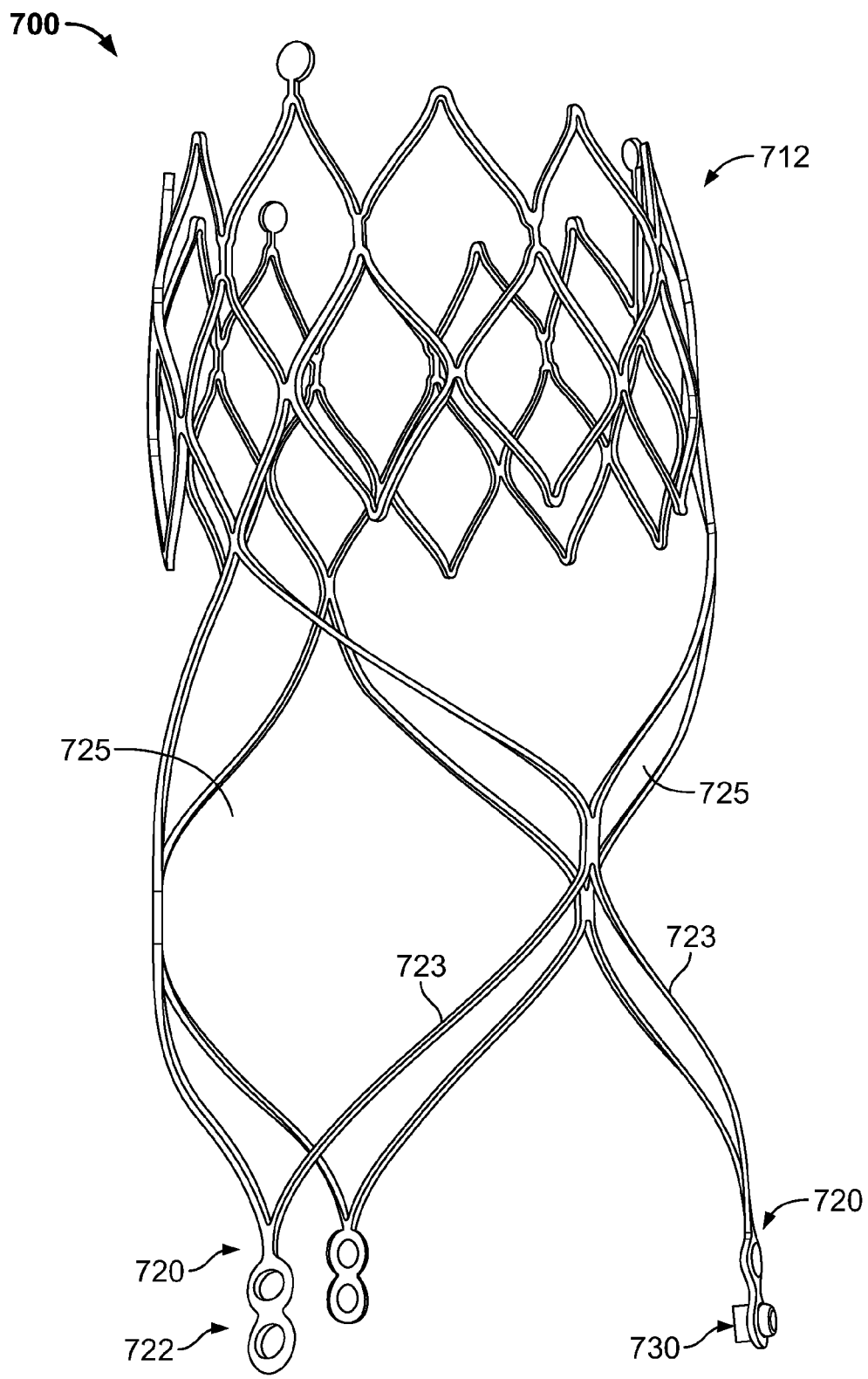
FIG. 7 is a front perspective view of yet a further embodiment of an expandable anchoring device having stent framed legs.

FIG. 7 depicts yet another expandable anchoring device 700. Anchoring device 700 includes an expandable annular body 712, attachment portions 722, and anchors 730 similar to those of anchoring device 10, but differs in that anchoring device 700 includes stent framed legs 720. Each leg 720 includes at least two struts 723 which are connected to one another and to body 712 at a first end, and connected to one another at a second end. The second end connection includes an attachment portion 722 which may include no anchors 730, or one or more anchors. Each strut 723 of one leg 720 is connected to a strut 723 of an adjacent leg 720. The struts 723 of each leg 720 define a cell 725 for that leg that is expandable and collapsible. The stent framed legs 720 may provide additional stability and support to the attachment portions 722 and/or anchors 730 when anchoring device 700 is implanted.

Figure 8:
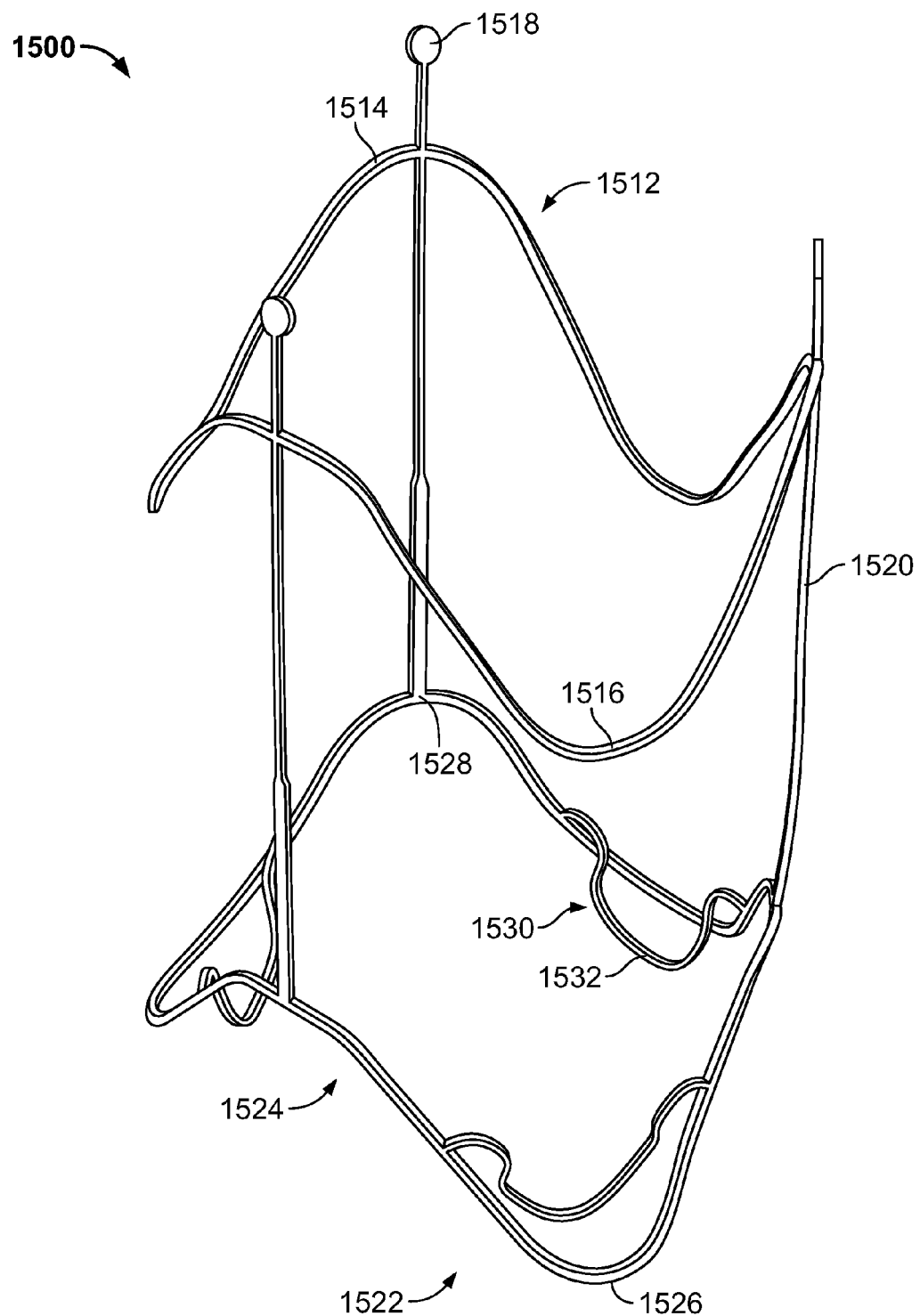
FIG. 8 is a front perspective view of another embodiment of an expandable anchoring device embodiment having alternative expandable body and anchor configurations.
Figure 9:
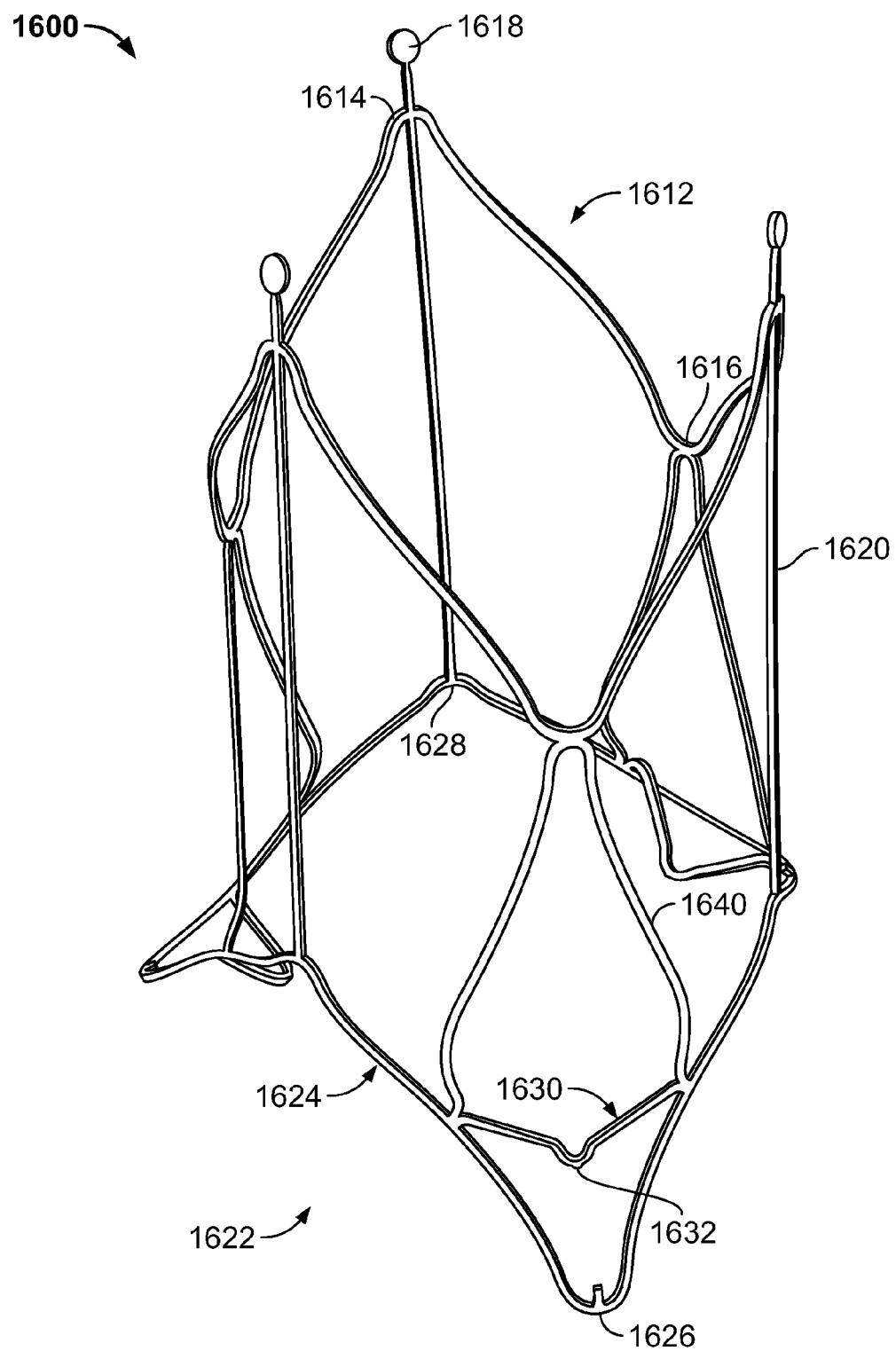
FIG. 9 is a front perspective view of another embodiment of an expandable anchoring device embodiment having support arms and alternative expandable body and anchor configurations.
Figure 10:
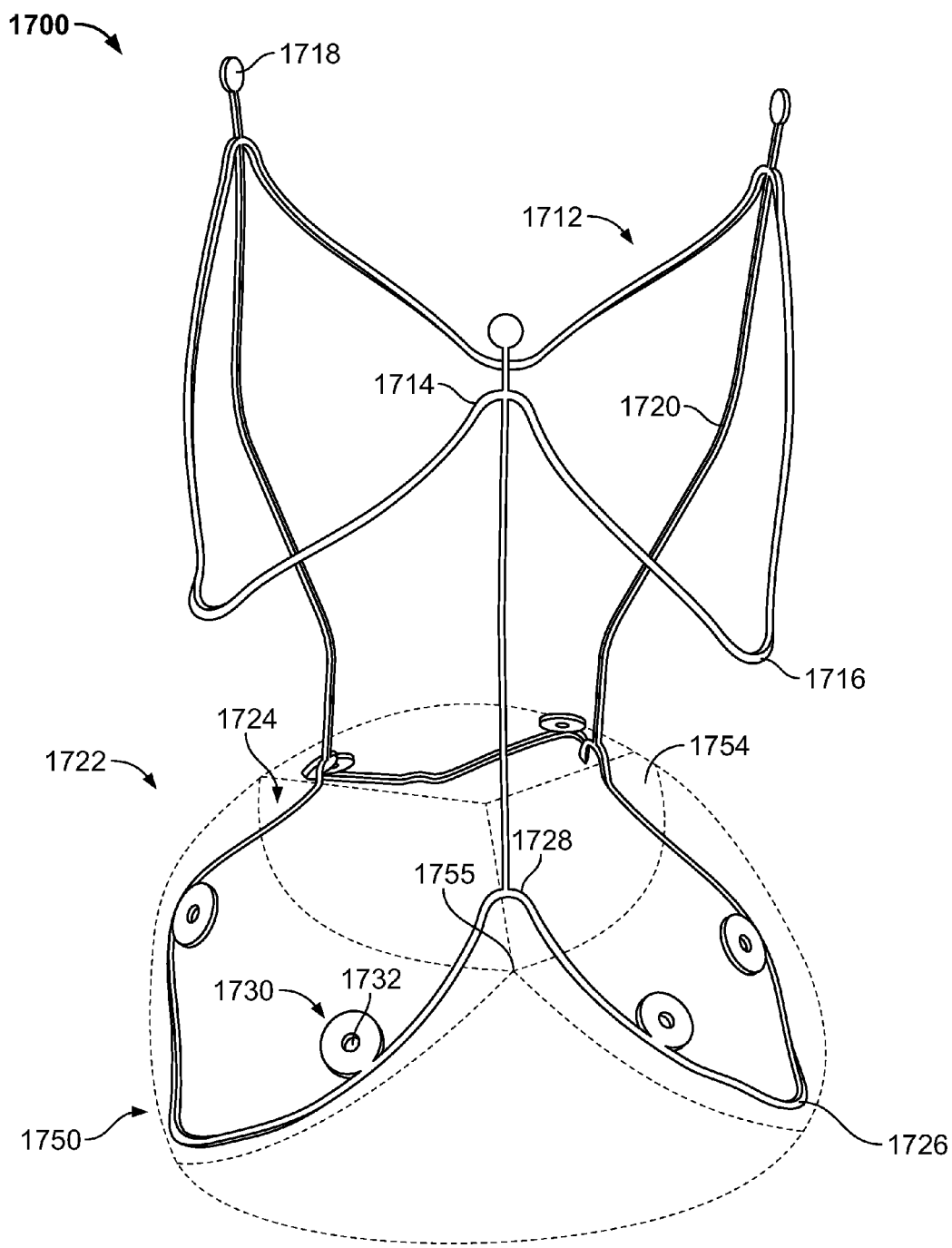
FIG. 10 is a front perspective view of another embodiment of an expandable anchoring device embodiment having anchor eyelets and alternative expandable body and anchor configurations.

FIGS. 8-10 depict alternative expandable anchoring devices. As previously mentioned in the description of anchoring device 10, the expandable body can be a stent comprised of a plurality of struts forming individually expandable cells. It was also described that the expandable body can be a wire-like structure collapsible in an accordion-like configuration. The embodiments of FIGS. 8-10 are exemplary of such wire-like expandable body structures. In addition, these embodiments are exemplary of alternative anchoring features.

FIG. 8 depicts anchoring device 1500, which generally includes an expandable body 1512, a plurality of legs 1520, and anchoring feature 1522. Anchoring device 1500 may be unsheathable from and resheathable within a delivery device, such as delivery device 40, for example. Further, anchoring device 1500 can optionally include retaining tabs 1518 to facilitate resheathability and to help maintain the anchoring device's orientation within the delivery device.

The expandable body 1512 may be form of a rounded or flattened wire of flexibly resilient material, such as Nitinol, stainless-steel, titanium, cobalt-chromium, biocompatible polymers, or the like, that is bent into the shape of a sine wave and formed into a closed ring. This closed ring is configured to conform to the aorta. As such, the peripheral profile of the expandable body 1512 is generally circular to conform to the tubular structure of the aorta.

The expandable body 1512 preferably has three peaks 1514 and three troughs 1516 forming the body's sine-wave-like structure. However, in some embodiments, expandable body 1512 may include 4 to 10 peaks and troughs, respectively. The sine-wave-like structure allows the expandable body 1512 to be collapsed like an accordion for placement within a delivery device while also being biased for radial expansion. Additionally, this structure provides torsional rigidity when fully expanded and deployed within an aorta while providing a lower profile than a closed-celled stent.

The anchoring feature 1522 includes a tripex anchoring ring 1524 and a plurality of anchors 1530. The tripex anchoring ring 1522 may be similar to expandable body 1512 in that the tripex anchoring ring 1524 may be formed of a rounded or flattened wire of flexibly resilient material that is bent into the shape of a sine wave and formed into an expandable closed ring. Unlike expandable body 1512, the tripex anchoring ring 1524 is configured for simultaneous placement within the ascending aorta and aortic root. The tripex anchoring ring 1524 preferably has three or more apices 1526 (or two or more apices for bicuspid valves) for placement within the aortic sinuses and three or more saddles 1528 (or two or more saddles for bicuspid valves) for straddling the commissures of the aortic valve at or adjacent to the sinotubular junction. The apices 1526 may flare out in a radially outward direction. Thus, the apices 1526 are located more distant from the central axis of the tripex ring 1524 than the saddles 1528. As such, the flaring of the apices 1526 allows for the tripex ring 1524 to conform to the vascular walls of both the ascending aorta and the aortic root simultaneously. In other words, the flaring of the apices 1526 allows the saddle region to conform to the tubular structure of the ascending aorta at or adjacent to the sinotubular junction, while the remainder of the tripex ring that is placed within the aortic sinuses can conform to the vascular structure as the tubular ascending aorta transitions to the more bulbous aortic root. This flaring feature provides resistance to migration in addition to the pinching effect.

The anchors 1530 are similarly formed of flexibly resilient flattened or rounded wires that connect to the tripex ring 1524 at two locations, each of which is located between an apex 1526 and an adjacent saddle 1528. Each anchor 1530 is depicted as having a shape similar to an upside down omega, which itself has an apex 1532 that is substantially aligned with an apex 1526 of the tripex ring 1524, but offset inwardly therefrom. This shape and alignment with the apices 1526 of the tripex anchoring ring 1524 allows the anchors 1530 to be expanded and collapsed in conjunction with the tripex ring 1524. When expanded, the anchors 1530 are angled slightly inward toward the central axis of the tripex ring 1524, which helps present the apices 1532 in a manner suitable for abutment with a transcatheter valve stent when fully implanted. When fully implanted, both the anchors 1530 and apices 1526 of the tripex ring 1524 are placed within the aortic sinuses, the apices 1526 of the tripex ring 1524 press against the vascular wall within the aortic root, and the anchors 1530 press against the valve leaflets to facilitate the pinching effect, as described more fully below.

The anchoring feature 1522 may be connected to the expandable body 1512 is connected to the anchoring feature 1524 by a plurality of legs 1520. Each leg 1520, as depicted, may connect to the tripex ring 1524 at a saddle 1528 and to the expandable body at a peak 1514. In some embodiments, the legs 1520 may each connect to the tripex ring 1524 at a saddle 1528 and to the expandable body 1512 at a trough 1516. The radius of the tripex anchoring ring 1524 at the saddles 1528 is substantially equal to the radius of the expandable body 1512. Therefore, regardless of where the legs 1520 connect to the expandable body 1512, they preferably connect to the tripex ring 1524 at the saddles 1528, which helps keep the legs 1520 relatively parallel to the longitudinal axis of anchoring device 1500. That in turn, helps the legs 1520 maintain consistent pressure along their respective lengths against the vascular wall of the aorta.

In a method of use, anchoring device 1500 is crimped and loaded into a delivery device, such as delivery device 40, for example. The delivery device is guided to a location downstream of the aortic valve where anchoring device 1500 is at least partially unsheathed. The apices 1526 of the tripex anchoring ring 1524 and/or the anchors 1530 can be coated with a radiopaque material for aiding in the alignment of the anchoring feature 1522 prior to implantation. As anchoring device 1500 is unsheathed, the independent expandability of the anchoring feature 1522 enables the tripex ring 1524 and anchors 1530 to at least partially expand while the expandable body 1512 remains within the delivery device. The legs 1520 are typically sufficiently flexible to bend to allow for this at least partial expansion. Once partially unsheathed, the alignment of the anchoring feature 1522 with respect to the aortic valve is assessed, and if necessary, anchoring device 1500 can be resheathed and its position adjusted.

Once the desired alignment is achieved, the anchors 1530 and apices 1526 of the tripex ring 1524 are inserted into the aortic sinuses, and the saddles 1528 are positioned to straddle the native valve commissures. Thereafter, anchoring device 1500 may be fully unsheathed and deployed into an anchoring position. In the anchoring position, the expandable body 1512 and legs 1520 press against the ascending aorta and the saddles 1528 press against the ascending aorta at or adjacent to the sinotubular junction. The tripex anchoring ring 1524 flares outwardly from the saddles 1528 into the aortic sinuses where each of the apices 1526 is centered behind a respective valve leaflet. The tapering between each apex 1526 and adjacent saddles 1524 results from the sine-wave-like structure of tripex ring 1524, which helps center the apices 1528 behind the leaflets as they are placed into the valve sinuses. The anchors 1530, at inwardly offset positions from the apices 1526 of the tripex ring 1524, are positioned within the native valve sinuses such that when a transcatheter valve is implanted, the anchors 1530 press against the native valve leaflets.

Once anchoring device 1500 has been implanted into this anchoring position, a transcatheter valve prosthesis may be guided to a position within the aortic valve where it is at least partially deployed. Positional alignment of the transcatheter valve is assessed with respect to the aortic valve. Resheathing of the transcatheter valve may occur when the valve is determined to be misaligned. Resheathing of the transcatheter valve would likely not be interfered with by the anchors 1530 due to their location behind the valve leaflets. Once the proper positioning is achieved, the transcatheter valve may be fully unsheathed and deployed. As previously mentioned, the anchors 1530 are slightly angled toward the central axis of the tripex ring 1524, which presents the apices 1532 to the transcatheter valve for abutment and interference with migration. Thus, in a fully anchored configuration, migration of the transcatheter valve and anchoring device 1500 is opposed by the pinching of the valve leaflets between the anchors 1530, particularly apices 1532, and the stent of the transcatheter valve. Migration may be further opposed by the conformity of the flared tripex ring 1524 with the vascular structure between the ascending aorta and aortic root.

FIG. 9 depicts expandable anchoring device 1600. Anchoring device 1600 is similar in some respects to anchoring device 1500. For example, anchoring device 1600 includes an expandable body 1612, a plurality of legs 1620, and an anchoring feature 1622 that includes a tripex anchoring ring 1624 and anchors 1630. In addition, the method of using anchoring device 1600 is substantially the same as that for anchoring device 1500. However, the expandable body 1612 and anchoring feature 1622 of anchoring device 1600 have different shapes than those in anchoring device 1500. Also, unlike anchoring device 1500, anchoring device 1600 includes support arms 1640. The expandable body 1612 may be formed of a rounded or flattened wire of flexibly resilient material, much like body 1512. However, expandable body 1612 is bent into the shape of a substantially triangular wave and formed into a closed ring. Due to the overall structure of anchoring device 1600, the peripheral profile of expandable body 1612 tends to be more triangular than that of body 1512. However, in an expanded state, expandable body 1612 is sufficiently curved at the periphery and flexible to conform to the tubular structure of the ascending aorta.

The expandable body 1612 preferably has three rounded peaks 1614 and three rounded troughs 1616 forming the body's triangle-wave-like structure. In some embodiments, expandable body 1612 may include 4 to 10 peaks and troughs, respectively. The triangle-wave-like structure allows the expandable body 1612 to be collapsed like an accordion for placement within a delivery device while also being biased for radial expansion. Additionally, this structure provides torsional rigidity when fully expanded and deployed within an aorta while providing a lower profile than a closed-celled stent.

The tripex anchoring ring 1624 may also be formed of a rounded or flattened wire that is bent along its length into the shape of a substantially triangular wave and formed into a closed ring. The tripex ring 1624 preferably includes three rounded apices 1626 (or two apices for bicuspid valves) for placement within the aortic sinuses and three rounded saddles 1628 (or two saddles for bicuspid valves) for straddling the commissures of the aortic valve at or adjacent to the sinotubular junction. The apices 1526 may flare radially outward from the saddles 1628 to facilitate conformity of the tripex ring 1624 with the vascular wall between the ascending aorta and the aortic root, as previously described in connection with anchoring device 1500. The tripex ring 1624 may also be tapered more steeply between each apex 1626 and adjacent saddles 1628 as compared to the taper of tripex ring 1524. Such steep taper helps form apices 1626 that are more pointed than apices 1526.

The anchors 1630 are attached to the tripex ring 1624 at two locations, each of which is located along the tripex ring 1624 between an apex 1626 and an adjacent saddle 1628. Each anchor includes an apex 1632 that is substantially aligned in a radial direction with an apex 1626 of tripex ring 1624, but canted radially inward toward the central axis of the tripex ring to facilitate the pinching effect. The apices 1632 of the anchors 1630 may also be more pointed in comparison to the apices 1532 associated with anchoring device 1500, which may be better suited for anchoring smaller celled transcatheter valves than anchoring device 1500.

The plurality of legs 1620 connect the tripex ring 1624 to the expandable body 1612. The tripex ring 1624 is further connected to the expandable body 1612 by support arms 1640. Each pair of support arms 1640 connects to a trough 1616 of the expandable body and then diverges to connect to the tripex ring 1624 on opposite sides of an apex 1626, generally between the apex 1626 and an adjacent saddle 1628. More particularly, in one embodiment, these connection locations can be the same as those that connect anchors 1630 to tripex ring 1624. In other embodiments, the support arms 1640 can connect to the tripex ring 1624 between the connection locations of anchors 1630 to tripex ring 1624 and an adjacent saddle 1628.

The support arms 1640 help provide stability and rigidity to anchoring device 1600. Additionally, the support arms 1640 help provide stiffness to the tripex ring 1624 and anchors 1630 to help prevent bending, collapsing, or buckling when anchoring a transcatheter valve. The enhanced support provided by arms 1640 may allow for a thinner wire frame than that of an anchoring device that does not include such arms. FIG. 10 depicts expandable anchoring device 1700. Anchoring device 1700 is similar in some respects to anchoring device 1600. For example, anchoring device 1700 includes an expandable body 1712 that has at least three peaks 1714 and three troughs 1716, and an anchoring feature 1722 that includes a tripex anchoring ring 1724 having three apices 1726 and three saddles 1728. The body 1712 and tripex ring 1724 may also be formed of a flexibly resilient wire configured into a closed loop triangular wave. Additionally, anchoring device 1700 includes a plurality of legs 1720 connecting the tripex ring 1724 to the expandable body 1712. However, unlike anchoring device 1600, anchoring device 1700 does not have support arms, although it may in some embodiments. Further, anchoring device 1700 includes attachment portions 1730 for attaching anchors, such as anchors 30 described above.

Each leg 1720 may attach to the expandable body 1712 at a peak 1714 and to the tripex ring 1724 at a saddle 1728. In some embodiments, the legs 1720 may attach to the expandable body 1712 at a trough 1716. Rather than being generally straight as in anchoring device 1600, legs 1720 bend radially inwardly along their respective lengths such that the portion of each leg 1720 that attaches to the tripex ring 1724 is offset inwardly from the portion that connects to the body 1712. This offset configuration of each leg 1720 positions the saddles 1728 closer to the central axis of the tripex ring 1724 as compared to anchoring device 1600, which gives the tripex ring 1724 a leaf-like appearance and helps maximize the length of the tripex ring 1724 between each saddle 1728 and an adjacent apex 1726. Where anchoring device 1600 tends to be more rigid at tripex ring 1624, particularly due to the support arms 1640, anchoring device 1700 tends to be more flexible at tripex ring 1724. Such flexibility is facilitated by the greater length between saddles 1728 and apices 1726 results from the offset configuration of the legs 1720.

The attachment portions 1730, which can be similar to attachment portions 22, each include at least one eyelet 1732 for attaching an anchor, such as anchor 30, thereto. As depicted by FIG. 10, an attachment portion 1730 may be connected to the tripex ring 1724 between each saddle 1728 and an adjacent apex 1726. Such configuration allows for an anchor to be connected to each attachment portion 1730, or to less than all of the attachment portions 1730. In other embodiments, multiple attachment portions 1730 may be connected to the tripex ring 1724 between each saddle 1728 and an adjacent apex 1726. In further embodiments, features from anchoring device 1600 may be combined with anchoring device 1700, for instance anchors 1630 and attachment portions 1730 may be connected to the tripex ring 1724. The attachment portions 1730 may be connected to the tripex ring 1724 either mechanically, such as by welding, or by forming the tripex ring 1724 and attachment portions 1730 together as an integral structure, such as by laser cutting the tripex ring 1724 and attachment portions 1730 together from a single piece of material.

In a method of using anchoring device 1700, a delivery device, such as delivery device 40, may be utilized to implant anchoring device 1700. As such, anchoring device 1700 may be crimped and loaded into the delivery device either in the operating room just before the procedure or during the manufacturing process and delivered to the operating room in a sterile pre-loaded configuration. The delivery device is introduced into the vascular system and guided to a location downstream of the aortic valve where anchoring device 1700 may be partially unsheathed to assess positional orientation and then resheathed to correct such positional orientation when desired. As anchoring device 1700 is partially unsheathed, the tripex ring 1724 is exposed first and flares outwardly while the expandable body 1712 remains within the delivery device. The apices 1726 may include radiopaque material to assist the operator in determining the position of the apices with respect to the valve sinuses 1754.

Once it is determined that the apices 1726 are aligned with the aortic valve sinuses 1754, the delivery device and anchoring device 1700 may be moved toward the aortic valve such that the saddles 1728 straddle the commissures 1755 and the apices 1726 and attachment portions 1730, and any anchors attached thereto, are placed within the valve sinuses 1754. As demonstrated by FIG. 10, the flaring of the apices 1726 radially outward from the saddles 1728 allows the tripex ring 1724 to conform to the outward taper of the vascular structure between the tubular aorta and more bulbous aortic root 1750. With the apices 1726 positioned within the aortic sinuses 1754 and the saddles 1728 positioned at or adjacent the sinotubular junction, the anchoring device 1700 may be fully unsheathed such that the expandable body 1712 presses against the aorta.

Thereafter, a transcatheter valve may be guided into position within anchoring device 1700 and the native aortic valve. The transcatheter valve may be partially unsheathed to assess for proper positioning and then resheathed to adjust positioning when desired. When correct positioning is achieved, the transcatheter valve may be fully unsheathed and implanted. As the valve expands, the stent of the transcatheter valve presses against the portion of the legs 1720 that is offset inwardly, which causes the saddles 1728 and legs 1720 to move outwardly and abut the vascular structure. The anchors press against the valve leaflets, which are then pinched between the anchors and the stent of the transcatheter valve, thereby anchoring the transcatheter valve and anchoring device in position.

Figure 11A:
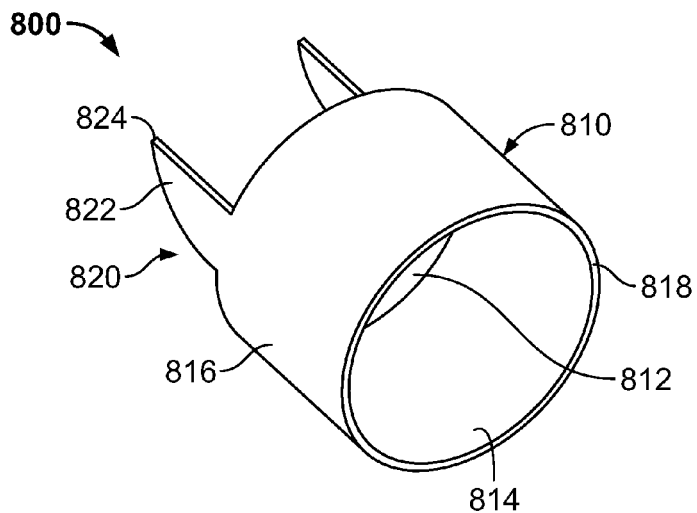
FIG. 11A is a perspective view of one embodiment of a stud-type anchoring device including a stud body and a mooring feature.

Shifting focus from expandable anchoring devices, FIG. 11A depicts a stud-type anchoring device 800. Anchoring device 800 includes a stud body 810 and one or more mooring features 820. The mooring feature 820 and stud body 810 may be made of any biocompatible material including, but not limited to titanium, stainless steel, cobalt-chromium, polymeric materials, and memory metal alloys, such as Nitinol.

The stud body 810 may have a generally cylindrical shape with an aperture 812 extending therethrough. The aperture 812 defines an inner surface 814 of the body 810 that is disposed opposite an outer surface 816 thereof. An edge 818 at one end of body 810 has a thickness defined by the distance between the inner surface 814 and outer surface 816.

The mooring features 820 may be in the form of tines 822 extending from the end of body 810 opposite edge 818. Anchoring device 800 may include one, two or more than two tines 822 extending from the end of body 810. Each tine 822 has a point 824 sufficiently sharp to penetrate soft tissue and may be configured to deform or bend upon penetration so as to prevent the tine 822 from being withdrawn from the vascular structure and from over-penetrating into adjacent structures. As an example, the tines 822 may be configured to bend toward one another or away from one another upon penetrating a valve leaflet or vascular wall.

The mooring features 820 and stud body 810 may be formed as a monolithic structure from a single piece of material such that the mooring features 820 are an extension of the stud body 810. For example, the mooring features 820 and stud body 810 may be laser cut from a single tube. In other embodiments, the mooring features 820 may be formed separately and attached to the stud body 810.

One aspect of the present disclosure includes a method for implanting a stud-type anchoring device, such as anchoring device 800, in the cardiovascular system. The method of implantation generally includes implanting at least one anchoring device 800 within at least one sinus of the target valve between a native valve leaflet and vascular wall. Thereafter, a transcatheter valve may be deployed within the diseased valve such that the native valve leaflet is pinched between the transcatheter valve and the implanted anchoring device 800.

Figure 11B:
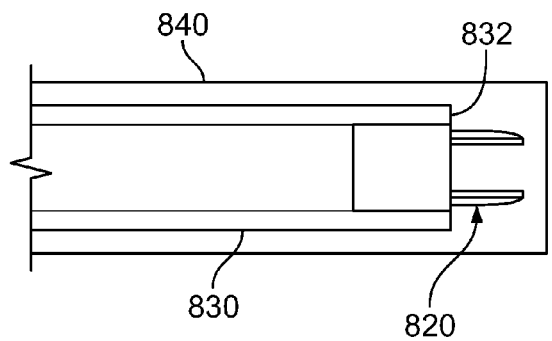
FIG. 11B is a partial cross-sectional view of a delivery device within a guide cannula, with the anchoring device of FIG. 11A attached to the delivery device.

FIG. 11B depicts an anchoring device 800 coupled to a delivery device 830 disposed within a guide cannula 840. Anchoring device 800 is coupled to the delivery device 830 such that the mooring features 820 extend in a longitudinal direction away from the end 832 of the delivery device 830. The guide cannula 840 helps guide the delivery device 830 to the target location with the patient's cardiovascular system and prevents the mooring features 820 from damaging the cardiovascular system as the delivery device 830 proceeds. anchoring device 800 is guided to the target location.

Figure 11C:
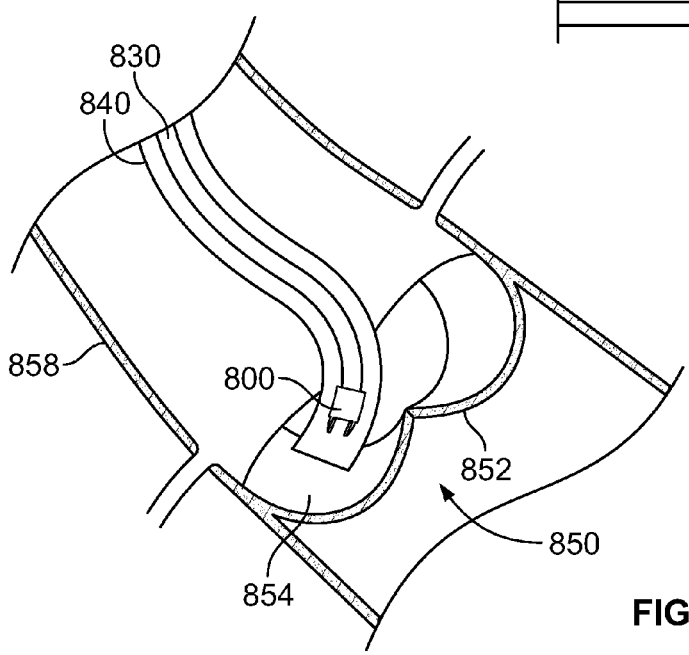
FIG. 11C is schematic view of the anchoring device of FIG. 11A being guided to a target location within the aorta.
Figure 11D:
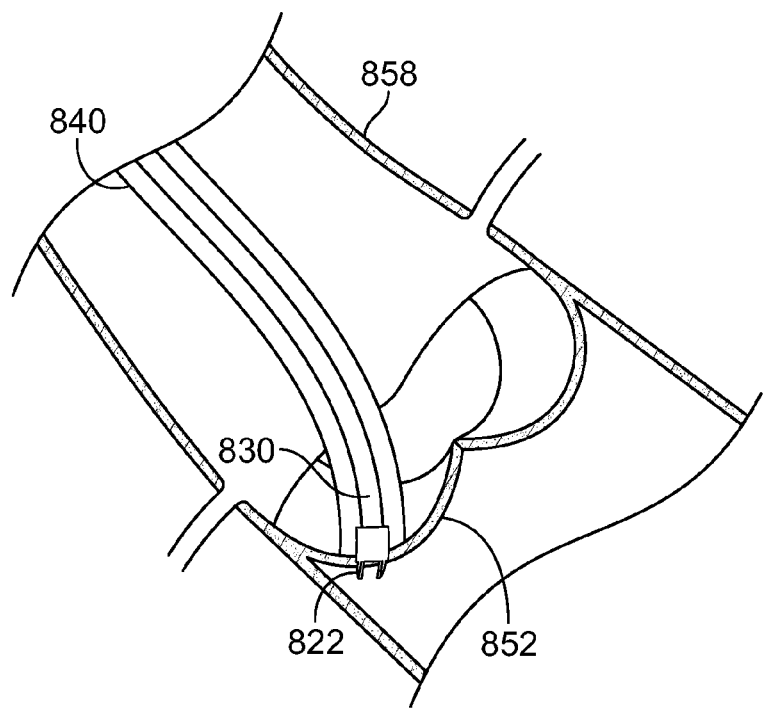
FIG. 11D is a schematic view of the anchoring device of FIG. 11A being implanted at a target location.
Figure 11E:
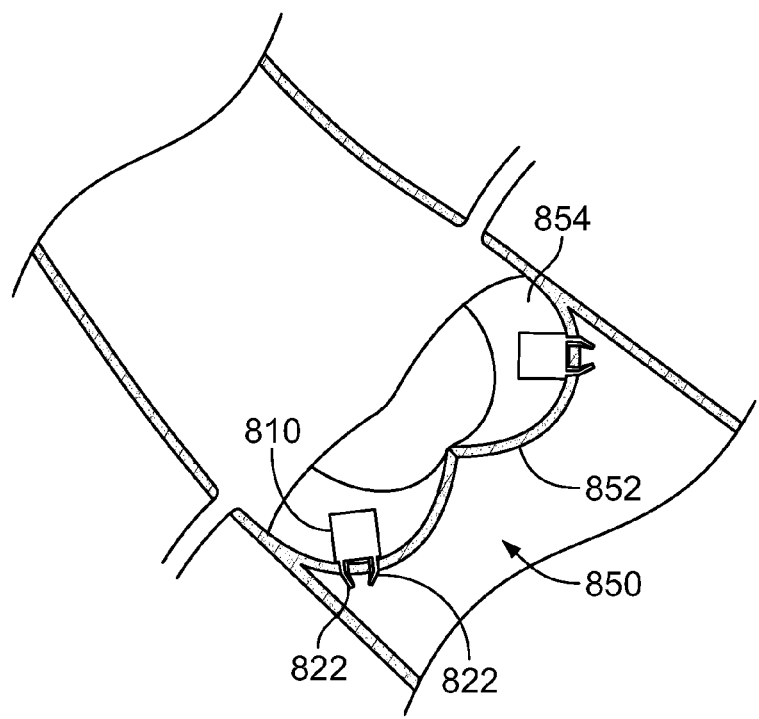
FIG. 11E is a schematic view of multiple ones of the anchoring device of FIG. 11A implanted at the target locations.

The method of delivering the anchoring device 800 to a target and implanting the anchoring device at the target is shown in FIGS. 11C-11E. To begin, the guide cannula 840 may be guided under radiography to the target location. Thereafter, the delivery device 830 is guided to the target location through the guide cannula 840, as shown in FIG. 11C. The target location is preferably a location within a sinus of the target valve 850, such as the right, left, or posterior aortic sinus. In one example, the target location may be on a valve leaflet 852 within a valve sinus 854 such that when anchoring device 800 is implanted, the tines 822 fully penetrate, or in some cases partially penetrate, the leaflet 852 from the outflow side to the inflow side of the leaflet, as shown in FIG. 11D. In another embodiment, the target location may be on the vascular wall 858 such that when anchoring device 800 is implanted, the tines 822 may completely or partially penetrate the vascular wall 858.

As depicted in FIG. 11E, as the tines 822 are passed into and/or through the valve leaflet 852, the tines 822 may bend inward toward each other. This may be achieved by constructing the tines 822 out of a memory metal material such that each tine 822 bends into an anchoring position after reaching an activation temperature following penetration of the vascular structure. For instance, the delivery device 830 and guide cannula 840 may be a part of a temperature control system that controls the temperature of anchoring device 800 until implantation, at which point anchoring device 800 is allowed to reach body temperature, thereby activating the tines 822. In another embodiment, the operator may deliver heat to anchoring device 800 at the moment activation of the tines 822 is desired.

Once the desired number of anchoring devices 800 have been implanted, a transcatheter valve prosthesis may be guided to the target valve 850 and partially deployed therein to assess for positioning and any paravalvular leaks. If repositioning is desired, the transcatheter valve prosthesis may be resheathed for further positional adjustments. When the anchoring device 800 is anchored to the native valve leaflets 852 and the tines 822 penetrate through the leaflets 852, the operator may need to make minor longitudinal movements of the transcatheter valve during resheathing to free the valve stent from any possible engagement with the bent tines 822. While the tines 822 penetrating the valve leaflets 852 may make resheathing potentially more difficult in that the valve stent may become snagged by the tines 822 during partial deployment, the portions of the tines 822 that extend from the leaflets 852 may help provide added anchoring support by providing an additional abutment surface for the strut of the transcatheter valve.

Once the proper positioning has been achieved, the transcatheter valve prosthesis may be fully deployed and anchored. When the transcatheter valve prosthesis is fully deployed and anchored, anchoring devices 800 function similarly to the anchors 30 of anchoring device 10. The stud body 810 provides bulk that helps pinch the native valve leaflet 852 between the body 810 and stent of the transcatheter valve and also helps push a portion of the native leaflet 852 through an adjacent stent cell to provide an abutment surface to corresponding struts of the stent in order to prohibit valve migration.

FIG. 12 illustrates an alternative stud-type anchoring device 900. Anchoring device 900 includes an alternative stud body 910 and one or more mooring features 920. The stud body 910 is similar to the stud body 810 of anchoring device 800 but differs in that the sidewall 918 is bent inward at one end of the body 910 to substantially close that end of the body and provide a smooth surface to reduce potential soft tissue irritation or damage. Alternatively, the body 810 can be deep drawn or solid throughout to eliminate edges at the tissue-anchoring device interface.

The mooring features 920 may be in the form of barbs 922 extending from the end of the stud body 910 opposite the substantially closed end. Anchoring device 900 may include at least two such barbs 922. Each barb 922 has a point 924 configured to penetrate the vascular structure and at least one backward facing point 926 configured to prevent back-out of the barb 922 and excessive damage to the underlying tissue.

FIG. 13 illustrates another alternative stud-type anchoring device 1000. Anchoring device 1000 is similar to anchoring device 800 but differs in that anchoring device 1000 includes a mushroom-shaped polymer insert 1030. The polymer insert 1030 includes a cylindrical shaft 1034 and an enlarged cap 1032. The cylindrical shaft 1034 is configured to fit within the stud body 1010 so that the cap 1032 extends from one end of the stud body 1010 and provides a smooth surface to help prevent tissue damage and/or irritation.

FIG. 14 illustrates a further stud-type anchoring device 1100. Anchoring device 1100 includes a stud body 1110 similar to stud body 810 of anchoring device 800 but differs with regard to the mooring feature. The mooring feature 1120 and stud body 1110 of anchoring device 1100 may be formed as a monolithic structure from a single piece of cylindrical material, such as a short length of hypotube. The stud body 1110 and mooring feature 1120 may be cut from this cylindrical material such that the mooring feature 1120 forms a threaded portion 1122 that includes a penetrating point 1124. The threaded portion 1122 and stud body 1110 may have the same outer diameter, with the threaded portion 1122 having a very shallow thread angle to help limit the total depth of penetration of the mooring feature 1120 while providing it with resistance to pull-out. The threaded portion 1122 may also include relatively wide gradually sloping surfaces 1126 to help spread pulling forces over a larger area once device 1100 has been implanted.

FIG. 15 illustrates still another stud-type anchoring device 1200. Anchoring device 1200 is similar to anchoring device 1100, but has an alternative embodiment of the mooring feature 1120. In device 1200, mooring feature 1220 is in the form of a helically coiled wire 1222 with a penetrating point 1224. The mooring feature 1220 may be formed separately from the study body 1210 and then attached thereto. The coils of mooring feature 1220 are generally concentric and become gradually smaller so that penetrating point 1224 is near the central axis of the stud body 1210. The coiled wire 1222 is coiled at a steeper angle than the threaded portion 1122 of anchoring device 1100, and therefore may penetrate tissue deeper than threaded portion 1122. However, as the coils of coiled wire 1222 have a smaller cross-section than the threads of threaded portion 1122, anchoring device 1200 may be less damaging to tissue than anchoring device 1100.

The anchoring devices of FIGS. 12-15 may be implanted in a substantially similar fashion as anchoring device 800, with the exception that anchoring devices 1100 and 1200 may be screwed into an implanted position and anchoring devices 800, 900 and 1000 may be pushed axially into an implanted position. Additionally, it should be understood that these embodiments are merely illustrative of the several mooring features and stud bodies that may be utilized. It should also be understood that any combination of the-features of these embodiments in a single device is possible without departing from the inventive concept.

Figure 16A:
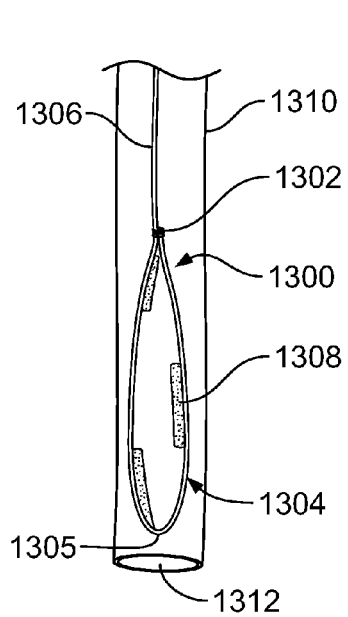
FIG. 16A is a partial cross-sectional view of a loop-type anchoring device loaded within a delivery cannula and including an anchoring loop.

Shifting focus from stud-type anchoring devices, FIG. 16A depicts a loop-type anchoring device 1300, which includes a single length of metal wire formed of Nitinol, stainless steel, titanium, cobalt-chromium or other biocompatible metal. The wire may be constructed as a rounded wire or a flat ribbon.

The wire may be passed through a sliding knot 1302 to form an anchoring loop 1304 and a free length 1306. The anchoring loop 1304 can be rounded so that when deployed, the loop 1304 will generally lie in a single plane. In other embodiments, the anchoring loop 1304 may be bent in various locations to form a loop configuration similar in appearance to the connected expander arms 640 of FIG. 6, which would facilitate placement of portions of the loop 1304 and anchors 1308 attached thereto within the aortic sinuses.

One or more anchors 1308 may be fixed to anchoring device 1300 along the anchoring loop 1304. In addition, the anchoring loop 1304 may include radiopaque markers to indicate the locations of the anchors 1308. The anchors 1308 may be expandable, and may include globules of hydrogel or fluid expandable balloons, for example. The globules of hydrogel may be expandable in volume up to about 300% and actuated by thermal stimuli. In one embodiment, the hydrogel globules may be expandable when exposed to a temperature of at least about degrees Celsius. Preferably, anchoring device 1300 includes at least one expandable anchor 1308 for each leaflet of the target valve.

As shown, anchoring device 1300 may be loaded into a delivery cannula 1310 for delivery to a target site. One of the many advantages anchoring device 1300 provides is a low profile delivery. The thin wire construction and looped configuration allows the anchoring device 1300 to be collapsed to a small cross-section and loaded in a delivery device 1310 having a relatively small diameter as compared to the other devices described herein.

A further aspect of the present disclosure includes a method of anchoring a stented device, such as a transcatheter valve prosthesis, utilizing anchoring device 1300. Such method generally includes guiding the anchoring loop 1304 to a location downstream of a target native valve and deploying it so that one or more of the anchors 1308 extend into a corresponding valve sinus. Thereafter, the anchors 1308 are expanded and a transcatheter valve prosthesis is deployed within the target valve such that the native valve leaflets are pinched between the anchors 1308 and the transcatheter valve.

Figure 16B:
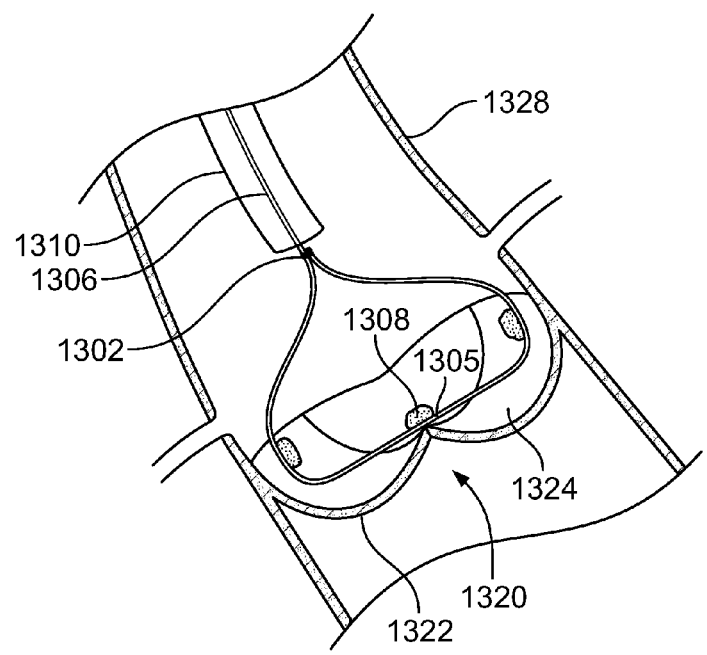
FIGS. 16B-16C are schematic views of the anchoring device of FIG. 16A being deployed and implanted at a target location within the aorta.
Figure 16C:
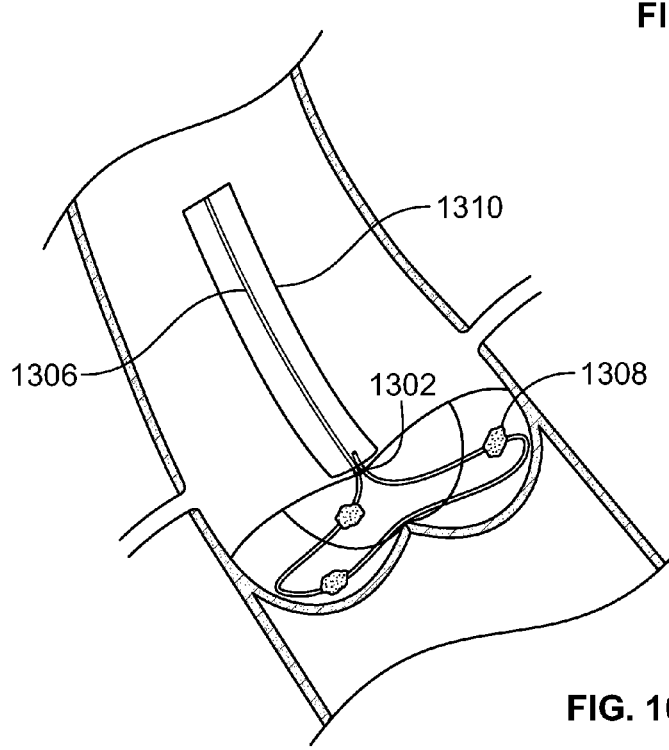

As depicted in FIG. 16A-16C, the delivery cannula 1310, including anchoring device 1300, is guided to a location downstream of the aortic valve 1320. The delivery cannula 1310 may be slightly bent such that the opening to the cannula 1310 projects towards the aortic wall 1328. The anchoring loop 1304 is then advanced out from the end 1312 of the delivery cannula 1310 where delivery cannula 1310 may then be manipulated until the apex 1305 of the anchoring loop 1304 contacts a vascular structure within the aorta, such as the aortic wall 1328 or a commissure. With the apex 1305 contacting the vascular structure, the loop 1304 is then expanded by further advancing the anchoring device 1300 out from the cannula 1310. As the apex 1305 of the loop 1304 is blocked by the vascular structure from further advancement, the loop 1304 begins to expand. The anchoring loop size may be adjusted by sliding the free end 1306 of anchoring device 1300 relative the sliding knot 1302, such as by a knot pusher (not shown). Alternatively, a knot pusher may be used to expand the loop 1304 independent of any contact of the apex 1305 with the vascular structure. Once the desired loop size is achieved, the delivery cannula 1310 can be manipulated and advanced further so that the loop 1305 is centered over the native valve 1320 and such that anchoring loop 1304 is placed adjacent the aortic leaflets 1322 with the anchors 1308 extending into the aortic sinuses 1324. Alternatively, at least a portion of the loop 1304 may extend into each sinus 1324, such as when the loop is bent as described above. Further size adjustments and positional adjustments may be made to obtain a snug fit against the aortic wall 1328 and to position each anchor 1308 in the desired location, preferably centered behind a respective valve leaflet.

Figure 16D:
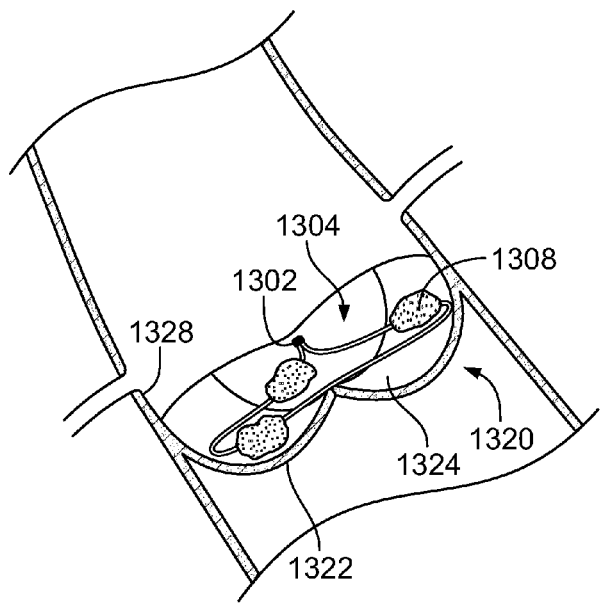
FIG. 16D is a schematic view of the anchoring device of FIG. 16A in a deployed state within the aorta.

Thereafter, the anchors 1308 may be expanded, as depicted in FIG. 16D. When the expandable anchors 1308 are globules of hydrogel, the free end 1306 of anchoring device 1300 may transfer heat from a heat source along its length to the anchoring loop 1304. Once the activation temperature is achieved, the anchors 1308 may permanently expand. A cutting device (not shown) may then be guided along the guide cannula 1310 to the sliding knot 1302, where the cutting device may cinch the knot 1302 and cut the free end 1306 away from the remainder of the anchoring device 1300.

Figure 16E:
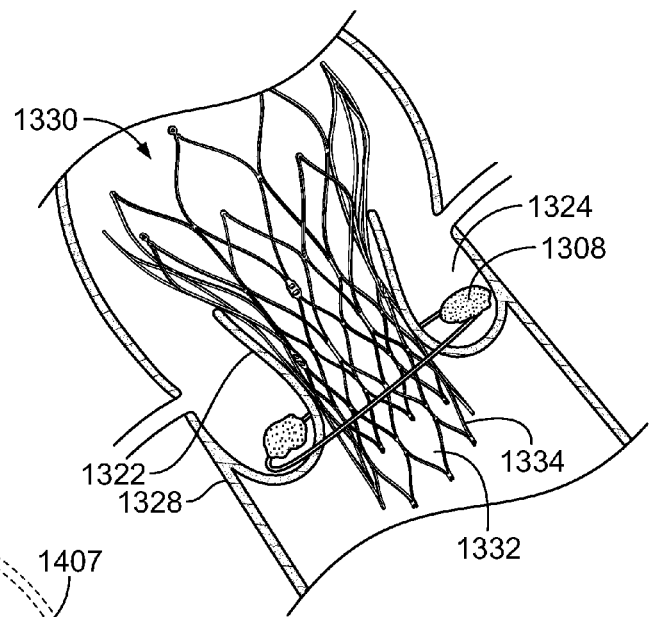
FIG. 16E is a schematic view of a transcatheter valve being deployed within the aortic valve with the anchoring device of FIG. 13A in the deployed state.

As shown in FIG. 16E, a transcatheter valve 1330 may be guided to the target valve and partially or fully deployed therein. As previously described in relation to anchoring device 10, the transcatheter valve 1330 may then be resheathed and repositioned if desired. Once the transcatheter valve 1330 is fully deployed and in an anchored position, at least one of the anchors 1308 will be disposed between a native valve leaflet 1322 and aortic wall 1328, with the native valve leaflet 1322 pinched between the transcatheter valve 1330 and anchor 1308 such that the anchor 1308 pushes a portion of the native leaflet 1322 into an adjacent cell 1332 of the transcatheter valve to provide an abutment surface for respective struts 1334 of the valve stent.

Figure 17:
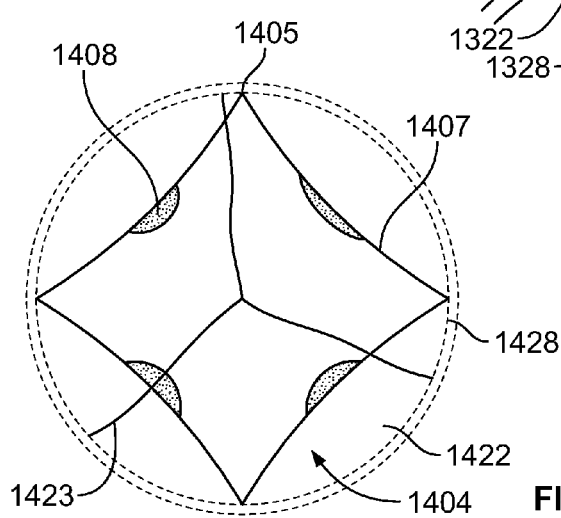
FIG. 17 is a highly schematic end view of an alternative embodiment anchoring loop deployed within the aortic sinus.

FIG. 17 depicts an alternative embodiment of the anchoring loop 1404. Anchoring loop 1404 may have a polygonal shape, such as a square or rectangle. Such shape can be prefabricated into a Nitinol wire. As shown, when implanted, the anchoring loop 1404 may contact the aortic wall 1428 at the corners 1405 of the loop 1404. Generally, the distances between opposite corners 1405 in a fully expanded anchoring loop 1404 is larger than the diameter of the aorta. However, the flexibility of the wire and the polygonal shape allows the sides 1407 of the loop 1404 to flex outwardly and/or inwardly and apply a force to the corners 1405 which helps the loop 1404 stay in position.

Expandable anchors 1408 may be positioned on each side 1407 of the loop 1404. As shown in FIG. 14 by the overlay image of the aortic valve leaflets 1422, such anchor configuration may place at least one expandable anchor 1408 within the commissure region 1423 of adjacent valve leaflets 1422 when implanted. This may allow the stent of the transcatheter valve to directly contact this expandable anchor 1408 and indirectly contact the remaining anchors 1408 through the valve leaflets 1422.

Moreover, although the anchoring devices herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the above-described embodiments and variations of the invention can be combined in ways other than as specifically described above. It is intended to cover all such variations which lie within the scope and spirit of the invention.

To summarize the foregoing description, an anchoring device for use within a cardiovascular structure, may include an expandable ring having a central axis extending in a longitudinal direction; a support structure extending from the expandable ring in the longitudinal direction; and at least one anchor coupled to the support structure and extending radially inwardly from the support structure toward the central axis; and/or
- the support structure may include a plurality of legs extending from the ring in the longitudinal direction, the plurality of legs may be arranged about the central axis of the ring; and/or
- each of the legs may have a length, the length of each of the legs may be different from the lengths of the other legs; and/or
- each of the legs may have a length, the length of each of the legs may be about the same; and/or
- each of the legs may have a twisted section and a straight section, the twisted section may include a first bend in a first direction and a second bend in a direction opposite the first direction to form an s-shape; and/or
- the plurality of legs may include a first bundle with at least two legs and a second bundle with at least two legs, the legs in the first bundle may be spaced closer to one another than to any of the legs in the second bundle, and the legs in the second bundle may be spaced closer to one another than to any of the legs in the first bundle; and/or
- the length of each leg within the first bundle may be different from the lengths of the other legs within the first bundle, and the length of each leg in the second bundle may be different from the lengths of the other legs within the second bundle; and/or
- at least one arm may extend from each of the legs at an oblique angle with respect to the longitudinal direction, the arm of one leg may connect to the arm of an adjacent leg at a node; and/or
- the support structure may further include at least two arms extending from each of the legs at an oblique angle with respect to the longitudinal direction, the arms of one leg may connect to the arms of an adjacent leg to form a closed cell; and/or
- the anchoring device may further include a plurality of anchors connected to at least one of the plurality of legs in a stacked arrangement in the longitudinal direction; and/or
- at least one of the plurality of anchors may be offset from the other anchors in a direction transverse to the longitudinal direction; and/or
- at least one of the plurality of legs may include a free end having at least one eyelet, and the anchor may include a body fixedly connected to the eyelet; and/or
- the body may have a prismatic, polygonal, or spherical shape; and/or
- the body may have at least one of a textured or polymer coated surface; and/or
- the anchor may include a polygonal-shaped frame attached to the support structure, the frame may have an aperture extending therethrough and being oriented at an angle transverse to the longitudinal direction; and/or
- the anchor may further include a finger connected to the frame and projecting into the aperture, the finger may be oriented at an angle transverse to the longitudinal direction and transverse to the frame; and/or
- the anchor may be a flat coil affixed to the support structure, the coil may be oriented in a radial direction toward the central axis of the ring; and/or
- the anchor may be a globule of hydrogel adapted to expand upon the application of heat to the hydrogel; and/or
- the anchor may be an expandable balloon; and/or
- the support structure may include a plurality of legs and an anchoring ring coupled to one end of the legs; and/or
- the anchoring ring may include a plurality of saddles and a plurality of apices, each of the legs may be attached to the anchoring ring at a saddle; and/or
- the support structure may further include at least one attachment portion coupled to the anchoring ring and may have at least one eyelet, the at least one anchor may include a body fixedly connected to the at least one eyelet; and/or
- the anchor may include an open frame having an apex, the open frame may be attached to the anchoring ring at at least two locations; and/or
- the expandable ring may be a stent having a plurality of struts defining a plurality of individual cells; and/or
- the expandable ring may be a wire-framed structure having a waveform geometry that may include at least one peak and at least one trough.

Also described was an anchoring device for use within a cardiovascular structure, which may include a cylindrical body having a first end, a second end, and a central axis extending in a longitudinal direction; and a mooring structure extending from the second end of the cylindrical body, the mooring structure having a penetrating point adapted to penetrate soft tissue and an anti-back-out feature disposed between the penetrating point and the second end of the cylindrical body; and/or
- the anchoring device may further include a polymeric body assembled to the first end of the cylindrical body so that a portion of the polymeric body projects outwardly from the first end; and/or
- the mooring structure may extend in the longitudinal direction and may have two conditions, wherein in the first condition the anti-back-out feature extends in the longitudinal direction, and the in the second condition the anti-back-out feature extends in a direction transverse to the longitudinal direction upon the application of one of heat or force to the mooring feature; and/or
- the mooring structure may extend in the longitudinal direction and the anti-back-out feature may include at least one barb protruding from the mooring structure and may have a retaining point projecting in a direction opposite the penetrating point; and/or the anti-back-out feature may include helical threads; and/or the cylindrical body may include a tubular wall, and the mooring structure may include two tines that are continuations of the tubular wall, each of the tines may taper from the second end of the cylindrical body to the penetrating point, the anti-back-out feature may include a first portion and a second portion, the second portion may be integral with the second end of the cylindrical body and the first portion may be disposed between the penetrating points and the second portion and bendable with respect to the second portion upon the application of one of heat or axial force to the first portion.

Also described was an anchoring device for use within a cardiovascular structure, which may include an expandable ring having a central axis extending in a longitudinal direction; a support structure extending from the expandable ring in the longitudinal direction and having at least one attachment portion; and at least one anchor connected to the at least one attachment portion; and/or the support structure may further include at least one leg having a first end connected to the expandable ring and a second end connected to the attachment portion; and/or the attachment portion may include an eyelet, and the anchor may include a head portion configured to fixedly engage to the eyelet; and/or the support structure may further include a plurality of legs and an anchoring ring, the plurality of legs may be connected to the expandable body at a first location and to the expandable ring at a second location, the at least one attachment portions may be connected to the anchoring ring.

Also described was an anchoring device for use within a cardiovascular structure, which may include a length of wire having a first portion with a free end, a loop formed at an end opposite the free end, and a sliding structure slidably connecting the loop to the first portion; and at least one anchor coupled to the length of wire along the loop, wherein a size of the loop is adjustable by sliding the first portion through the sliding structure; and/or the at least one anchor may be a globule of hydrogel adapted to expand upon the application of heat to the hydrogel; and/or the at least one anchor may be an expandable balloon; and/or the loop may have four sides and four corners, and at least one anchor may be coupled to each of the sides.

Also described was a method of anchoring a transcatheter valve prosthesis in a cardiovascular structure for replacing a native valve. The transcatheter valve prosthesis may include an expandable stent having a plurality of individually expandable cells. The method may include introducing into the cardiovascular structure a first delivery device having an anchoring device therein in a contracted configuration. The anchoring device may include an expandable ring having a central axis extending in a longitudinal direction, a support structure extending from the expandable ring in the longitudinal direction, and at least one anchor coupled to the support structure and extending radially inwardly from the support structure. The method may also include the steps of guiding the first delivery device to a deployment location downstream of the native valve; and deploying the anchoring device from the first delivery device such that the at least one anchor is positioned within a sinus of the native valve.

Additionally, the method may include the steps of guiding a second delivery device containing the transcatheter valve prosthesis to the native valve; and deploying the transcatheter valve prosthesis from the second delivery device within the native valve such that a portion of a leaflet of the native valve is pinched between the at least one anchor and the transcatheter valve prosthesis; and/or the step of deploying the anchoring device may include partially deploying the anchoring device from the first delivery device in a first position; assessing the first position of the anchoring device with respect to the native valve; resheathing the anchoring device within the first delivery device; repositioning the first delivery device to a second position relative to the native valve; and partially deploying the anchoring device from the first deliver device in the second position; and/or the anchoring device may include at least two anchors, and the step of deploying the anchoring device may include positioning at least one of the anchors within a commissure region of the native valve; and/or the step of deploying the transcatheter valve prosthesis may include deploying the transcatheter valve prosthesis so that the at least one anchor projects into one of the individually expandable cells; and/or the support structure may include a plurality of legs, an expander arm assembly disposed between an adjacent pair of the legs and having a first arm connected to one of the adjacent pair of legs at an oblique angle relative to the longitudinal direction, and a second arm connected to another of the adjacent pair of legs at an oblique angle to the longitudinal direction, the first arm may be connected to the second arm at a node. The step of deploying the anchoring device may include positioning the node within the sinus of the native valve; and/or the support structure may include an anchoring ring having a plurality of saddles and plurality of apices, and the method may further include the steps of positioning the plurality of apices in the sinus of the native valve and positioning the plurality of saddles in straddling positions over commissures of the native valve.

Also described was a method of positioning an anchoring device within a cardiovascular structure, which may include introducing into the cardiovascular structure a delivery device having an anchoring device therein in a contracted configuration. The anchoring device may include an expandable ring having a central axis extending in a longitudinal direction, a support structure extending from the ring in the longitudinal direction, and at least one anchor coupled to the support structure and extending radially inwardly from the support structure. The method may also include the steps of guiding the delivery device to a deployment location downstream of a native valve; and deploying the anchoring device from the delivery device such that the at least one anchor is positioned within a sinus of the native valve; and/or the deploying step may include partially deploying the anchoring device from the delivery device in a first position; assessing the first position of the anchoring device with respect to the native valve; resheathing the anchoring device within the delivery device; repositioning the delivery device to a second position relative to the native valve; and partially deploying the anchoring device from the delivery device in the second position; and/or the anchoring device may include at least two anchors, and the deploying step may include positioning at least one of the anchors within a commissure region of the native valve; and/or the support structure may include a plurality of legs, an expander arm assembly disposed between an adjacent pair of the legs and having a first arm connected to one of the adjacent pair of legs at an oblique angle relative to the longitudinal direction, and a second arm connected to another of the adjacent pair of legs at an oblique angle to the longitudinal direction. The first arm may be connected to the second arm at a node. Also, the displaying step may further include positioning the node within the sinus of the native valve; and/or the support structure may include an anchoring ring having a plurality of saddles and a plurality of apices, and the method may further include positioning the plurality of apices in the sinus of the native valve and positioning the plurality of saddles in straddling positions over the commissures of the native valve.

The invention claimed is:

1. An anchoring device for use within a cardiovascular structure, comprising:
    a first radially expandable ring having a central axis extending in a longitudinal direction;
    a plurality of legs extending from the first expandable ring in the longitudinal direction, each of the legs having first and second ends;
    a second radially expandable ring forming a set of apices that point in a direction away from the first expandable ring, the second expandable ring being connected to each of the legs between the first and second ends thereof so that a portion of each of the legs extends from the second expandable ring between adjacent ones of the apices; and
    an anchor connected to each of the legs and extending radially inwardly therefrom toward the central axis.

2. The anchoring device of claim 1, wherein the cardiovascular structure is a heart valve having a predetermined number of leaflets and the plurality of legs are equal in number to the predetermined number.

3. The anchoring device of claim 1, wherein the second expandable ring forms a set of second apices that point in a direction toward the first expandable ring, and each of the legs intersects a corresponding one of the second apices.

4. The anchoring device of claim 1, wherein each of the anchors is connected to the portion of one of the legs.

5. The anchoring device of claim 1, wherein the first end of each of the legs is connected to the first expandable ring and the portion of each of the legs comprises the second end of the leg.

6. The anchoring device of claim 5, wherein the second end of each of the legs includes an attachment portion connected thereto, and the anchor is connected to the attachment portion and includes a body extending radially inwardly from the attachment portion.

7. The anchoring device of claim 6, wherein the attachment portion includes an eyelet, and the anchor includes a deformable head portion fixedly engaged to the eyelet.

8. The anchoring device of claim 6, wherein the body has a prismatic, polygonal, or spherical shape.

9. The anchoring device of claim 1, wherein each of the anchors is connected to the second end of one of the legs.

10. An anchoring device for use within a cardiovascular structure, comprising:
    a stent body having a central axis extending in a longitudinal direction;
    a plurality of legs extending from the stent body in the longitudinal direction, each of the legs having a first end connected to the stent body and a second end remote from the stent body;
    a ring connected to each of the legs between their respective first and second ends and forming a plurality of apices pointing in the longitudinal direction away from the stent body; and
    an anchor connected to one of the legs and extending radially inwardly therefrom toward the central axis.

11. The anchoring device of claim 10, wherein the at least one of the legs includes an attachment portion defining an eyelet, and the anchor includes a head portion fixedly engaged to the eyelet.

12. The anchoring device of claim 10, wherein the apices are disposed further from the stent body than the second end of each of the legs.

13. The anchoring device of claim 10, wherein each of the apices is disposed between adjacent ones of the legs.

14. The anchoring device of claim 10, wherein the anchor is connected to the one leg between the second end thereof and the ring.

15. An anchoring device for use within a cardiovascular structure, comprising:
    a radially expandable ring having first and second ends and a longitudinal axis extending therebetween and defining a longitudinal direction; and
    first and second legs each extending from the expandable ring to a free end, the first leg including a first elongate member extending in a direction transverse to the longitudinal direction, the second leg including a second elongate member extending at least partially in a direction transverse to the longitudinal direction, the first and second elongate members converging and connecting to one another to form an angle therebetween and being flexible such that the angle formed therebetween is variable, the free end of the first leg having an anchor connected thereto, the anchor extending from the free end of the first leg radially inwardly toward the longitudinal axis.

16. The anchoring device of claim 15, wherein the connection of the first elongate member to the second elongate member forms an apex at a location further from the expandable ring in the longitudinal direction than the free ends of the first and second legs.

17. The anchoring device of claim 16, wherein the free end of the first leg includes an attachment portion having an eyelet, and the anchor is connected to the eyelet.

18. The anchoring device of claim 15, wherein the first and second elongate members converge at a location disposed between the free ends of the first and second legs and the expandable ring, the first and second elongate members at least partially defining an expandable cell.

19. The anchoring device of claim 18, wherein the free end of the first leg includes an attachment portion having an eyelet, and the anchor includes a head portion deformable to fixedly engage to the eyelet.

* * * * *